(12) United States Patent
Van Alstine et al.

(10) Patent No.: US 9,624,262 B2
(45) Date of Patent: Apr. 18, 2017

(54) PLASMA PROTEIN FRACTIONATION BY SEQUENTIAL POLYACID PRECIPITATION

(75) Inventors: James Van Alstine, Uppsala (SE); Mikael Berg, Uppsala (SE); Johanna Kjorning, Stockholm (SE); Jamil Shanagar, Uppsala (SE)

(73) Assignee: GE Healthcare BioProcess R&D AB, Uppsala (SE)

( * ) Notice: Subject to any disclaimer, the term of this patent is extended or adjusted under 35 U.S.C. 154(b) by 109 days.

(21) Appl. No.: 14/345,302

(22) PCT Filed: Sep. 14, 2012

(86) PCT No.: PCT/SE2012/050971
§ 371 (c)(1),
(2), (4) Date: Mar. 17, 2014

(87) PCT Pub. No.: WO2013/039449
PCT Pub. Date: Mar. 21, 2013

(65) Prior Publication Data
US 2014/0343253 A1 Nov. 20, 2014

(30) Foreign Application Priority Data
Sep. 16, 2011 (SE) ...................................... 1150842

(51) Int. Cl.
| | |
|---|---|
| *C07K 1/30* | (2006.01) |
| *C07K 14/75* | (2006.01) |
| *C07K 14/76* | (2006.01) |
| *C07K 14/765* | (2006.01) |
| *C07K 16/06* | (2006.01) |
| *C07K 16/18* | (2006.01) |
| *A61K 35/16* | (2015.01) |

(52) U.S. Cl.
CPC .............. *C07K 1/30* (2013.01); *C07K 1/303* (2013.01); *C07K 14/75* (2013.01); *C07K 14/76* (2013.01); *C07K 16/18* (2013.01); *A61K 35/16* (2013.01)

(58) Field of Classification Search
None
See application file for complete search history.

(56) References Cited

U.S. PATENT DOCUMENTS

| | | |
|---|---|---|
| 3,555,001 A | 1/1971 | Wallis et al. |
| 7,879,332 B2 | 2/2011 | Zurlo et al. |

FOREIGN PATENT DOCUMENTS

| | | |
|---|---|---|
| WO | 84/03628 | 9/1984 |
| WO | 86/05190 | 9/1986 |
| WO | WO 2010-080062 | 7/2010 |
| WO | WO 2010-082894 | 7/2010 |

OTHER PUBLICATIONS

Zhang et al. "Lysozyme purification from tobacco extract by polyelectrolyte precipitation" J. Chromatography, 1069:107-112 (2005).
Azevedo, A., et al., Trends in Biotechnology, vol. 27, No. 4, 2009, pp. 240-247.
Burnouf, T., Transfusion Medicine Reviews, vol. 21, No. 2, 2007, pp. 101-117.
Carlsson, F., et al., J. Phys. Chem. B., 105, 2001, pp. 9040-9049.
Carrette, O., et al., Nature Protocols, vol. 1, No. 2, 2006, pp. 812-824.
Cohn, E., J., et al., Separation into Fractions of Protein and Lipoprotein Components, 1946, pp. 459-475.
Johansson, H., et al., Biotechnology and Bioengineering, vol. 66, No. 4, 1999, pp. 247-257.
Johansson, H., et al., Journal of Chromatography B, 711, 1998, pp. 3-17.
Lee, Y., et al., J. Agric. Food Chem., vol. 35, No. 6, 1987, pp. 958-962.
Lihme, A., et al., Analytical Biochemistry, 399, 2010, pp. 102-109.
Ma, J., et al., Journal of Chromatography B, 862, 2008, pp. 219-226.
McDonald, P., et al., Biotechnology and Bioengineering, vol. 102, No. 4, 2009, pp. 1141-1151.
Peram, T., et al., Biotechnol. Prog., vol. 26, No. 5, 2010, pp. 1322-1331.

(Continued)

*Primary Examiner* — Marsha Tsay
(74) *Attorney, Agent, or Firm* — Wood IP LLC

(57) ABSTRACT

There is a recognized need for novel, more simplified, approaches to isolation of plasma from whole blood, as well as a need to isolate cell-free plasma fractions containing different plasma proteins. Methods are divulged for use of aqueous phase systems, formed in blood or blood containing solutions via addition of a single polymer at relatively low concentration, to effect isolation (clarification) of plasma proteins from blood cells. Methods are also divulged to replace widely used Cohn-type plasma protein fractionation which is based on sequential addition of up to 40% (v/v) ethanol and other precipitants, with simple sequential addition of a polyacid. The latter results in isolation of plasma protein fractions (i.e. fibrinogen, immunoglobulin, albumin) in sequence similar to that obtained with Cohn Fractionation and therefore may be suitable for use to reduce solvent use and solvent-related process complications in existing plasma protein purification processes. It may also support use of polymeric film based containers in novel solvent free plasma fractionation processes. The methods disclosed may also be suitable for use in smaller scale plasma protein isolation, in research and diagnostic applications. The general methodologies are robust and can function over a broad range of process variables such as temperature and pH.

25 Claims, 18 Drawing Sheets

(56) References Cited

OTHER PUBLICATIONS

Roush, D., et al., Biotechnol. Prog., vol. 24, No. 3, 2008, pp. 488-495.
Thommes, J., et al., Biotechnol. Prog., vol. 23, No. 1, 2007, pp. 42-45.
Venkiteshwaran, A., et al., Biotechnology and Bioengineering, 2008, pp. 1-10.

PLASMA PROTEIN FRACTIONATION BY SEQUENTIAL POLYACID PRECIPITATION

CROSS-REFERENCE TO RELATED APPLICATIONS

This application is a filing under 35 U.S.C. 371 of international application number PCT/SE2012/050971, filed Sep. 14, 2012, published on Mar. 21, 2013 as WO 2013/039449, which claims priority to application number 1150842-1 filed in Sweden on Sep. 16, 2011.

TECHNICAL FIELD OF THE INVENTION

The present invention relates to separation of blood components. In particular it relates to a process for fractionation of blood plasma into pharmaceutically useful components.

BACKGROUND OF THE INVENTION

Non-Chromatographic Methods for Macromolecule Isolation and Purification

Producers of plasma proteins from natural sources have long depended on ethanol based differential protein precipitation to sequentially isolate protein fractions prior to purification of individual proteins via column chromatography. Such approaches are particularly suited to larger scale separations run with tight production economies. However, they are technically complex and require highly trained technicians and expensive equipment and facilities.

Scientists involved in biotechnical separation processes are dealing with ever larger processes and the need to reduce the costs of produced goods. They are re-examining the use of techniques such as precipitation and partitioning in aqueous two-phase systems (1, 2, 3). The main advantage of partition is that it is based on formation of two liquid (L) phases such that cells and cell debris can be collected at the L-L phase interface where they are held by interfacial tension. Thus if target protein can be partitioned to a significant degree into one of the phases, in a selective manner, it is possible to effect some degree of target clarification (cell debris removal), purification, and concentration all in one step (above refs.). The major disadvantage to partition is that formation of aqueous polymer two phase systems typically require adding either two polymers such as dextran and polyethylene glycol [PEG] or adding one polymer and a high concentration of salt (e.g. PEG and 0.5M phosphate) to target containing solutions. The two polymer systems can be expensive and the polymer-salt systems have low capacity (solubility)—often 1 to 2 g/L for antibody proteins (3). An approach to clarify biotechnical feeds by adding relatively low concentrations of a single biocompatible thermotropic polymer has recently been disclosed (4), which allows for clarification via formation of an essentially polymer-free phase, which contains most protein, and typically floats on top of a denser polymer-rich lower phase. The upper phase can also be modified via addition of precipitating agents so as to effect further concentration and purification of target.

Single Polymer Aqueous Two-Phase Systems

It has long been known that proteins can be selectively partitioned between the phases of aqueous polymer two phase systems formed spontaneously using two polymers such as dextran and polyethylene glycol or one polymer such as PEG and relatively high concentrations of a water structuring salt such as NaPhosphate. The latter systems are less expensive however they tend to have lower protein solubility and thus capacity (3, 4). It has also long been appreciated that cells and cell debris, and other micron sized colloids, tend to accumulate at the interface of the two phases where they are held by interfacial tension. One variant of the above two types of LL systems has been polymer-polymer systems where one polymer is a thermo-responsive polymer which self associates under elevated temperature and other conditions (3, 4). This behaviour has previously been used, following phase separation and isolation of the two phases, to isolate proteins from polymer in one of the phases, and recover phase polymer for re-use. In addition to those two types of phase systems a third type has been recognized—single polymer systems. These are formed under conditions where added hydrophilic polymer self-associates and in so doing forms a lighter polymer-poor phase floating on top of a much denser polymer-rich phase (4, 5). Suitable polymers include so called "EOPO" polymers (e.g. Pluronic®, Tergitol®, Breox® families) made from ethylene oxide (EO) and propylene oxide (PO) components. Other suitable polymers may include cellulose or other polysaccharide polymers secondarily modified with ethoxy containing groups. From a bioseparations perspective a major drawback of such single polymer, low salt, two-phase systems has been that proteins tend to partition without any selectivity into the upper (polymer poor) phase. Hence it has been written that "the water-EOPO system is therefore only suitable for partitioning of hydrophobic molecules (such as denatured proteins or tryptophan rich peptides or for solution concentration by selective water removal" (5). One possible academic solution was to modify EOPO polymers hydrophobically (6), however that may lead to detergency and other complications. It was recently discovered that EOPO polymers could be added directly to fermentation broths, taking advantage of the fermentation temperature and salts, to effect formation of a two-phase system where cell debris would be concentrated at the phase interface and soluble substances, such as proteins, would partition into the polymer-poor phase where they could then be readily filtered and chromatographed (4). This work was focussed on fermentations related to recombinant proteins in general and monoclonal antibody production in particular.

Protein Precipitation

While flocculation and precipitation (terms considered equivalent herein) have been proposed for cell debris removal (2) they also pose some attractiveness for processing bioprocess feeds pre-clarified using the classical approach of centrifugation followed by filtration (1, 2, 7-12). In those scenarios target purification may be effected by precipitation of contaminants such as host cell proteins (HCPs). Fortuitously most monoclonal antibodies, and many naturally occurring antibodies in blood, are net positively charged at pH 7, while many HCPs and nucleic acid contaminants are net negatively charged (7). Thus a polycationic polymer can be used to precipitate many HCPs and nucleic acid contaminants leaving net positively charged target monoclonal antibody (Mab) proteins in solution (8, 10). Alternatively one may wish to use net negatively charged polymers to precipitate net positively charged Mab targets and leave net negatively charged proteins and nucleic acids in solution (7-9). In both cases some form of filtration, centrifugation or other methodology is required to isolate the precipitate from the supernatant (11).

One advantage of precipitating an antibody or other target protein is that the target may be quite stable in the precipitate, and thus able to be stored intermittently during processing (12,13). A disadvantage is that dissociating the precipitate and re-solubilising the target protein (e.g. for follow-on purification via chromatography) can require diluting the protein which increases process volumes (e.g. 8). It may also require resuspension in buffers whose conductivity, pH or other properties are not commensurate with processing by chromatographic or other desired separation methods. An approach to purify biotechnical proteins such as Mabs and related antibody fragments (Fabs) using polycarboxylic acid in the presence of salts such as sodium citrate has recently been disclosed (7).

In the above examples pH was typically controlled to effect a situation where the substance to be precipitated had an opposite net charge to the precipitant it interacted with. Similar considerations apply if proteins such as antibodies are preferentially precipitated using salts such as ammonium sulphate, again using control of pH to ensure that antibodies are have opposite net charge to major contaminants (11). This helps ensure the protein is associated in complexes where it is charge neutral. When precipitants are uncharged, such as in the case of solvents like ethanol, or neutral (uncharged) polymers such as polyethylene glycol, control of solution pH to match the pH of isoelectric charge (pI) of the target protein is often very effective (12). This is because the precipitants typically bind water molecules and reduce target solvation.

Ethanol (14,15) and salts (22) have both been used to separate complex protein mixtures into several fractions by sequential precipitation, where one protein fraction after another is precipitated and recovered as the concentration of the precipitating agent is increased. This is possible because a) different proteins precipitate at different precipitant concentrations and b) once a particular protein has been precipitated, it is remains insoluble when the precipitant concentration is increased further. Precipitation with charged polymers as in (8,10) has however not been used for fractionation by sequential precipitation, as the precipitates tend to redissolve upon addition of an excess of precipitant polymer (8,9,10). This behaviour makes it essentially impossible to control a sequential precipitation process when two or more target proteins exhibit significantly different solubilities.

Plasma Protein Fractionation

Plasma is an invaluable source of relatively inexpensive therapeutic proteins; especially in developing countries. Every year several billion dollars of plasma proteins are isolated and sold for therapeutic uses. The major proteins of interest are those which are abundant in reasonably high concentration in plasma and include albumin, fibrinogen and various immunoglobulins such as those belonging to the IgG, IgA, and IgM classes. However other proteins such as clotting factors V, VII, VIII, IV and von Willebrand factor (vWF), as well as transferrin, fibronectin, and alpha-1-antitrypsin, are of growing commercial significance (14, 15).

TABLE 1

Some Abundant Human Plasma Proteins

| Protein | Mw (kDa) | pI | Plasma (g/l) |
|---|---|---|---|
| Serum albumin | 69 | 5.6 | 35-55 |
| Immunoglobulin | 145-190 | 6.5-9.5 | 14 |
| Fibrinogen | 340 | 5.1-6.3 | 1.5-3 |
| Transferrin | 80 | 5.6-6.0 | 2.3 |
| Factor VIII | 280 | 5-6 | 0.20 |

In general donated blood is centrifuged to generate cell-rich fractions and plasma. A need for large scale centrifugation and sterility can limit the flexibility of such processes. Plasma is often stored frozen. Plasma proteins are purified based on chromatographic treatment of fractions which are first isolated using a general method termed Cohn Fractionation. It which was first developed by Cohn et al in the United States during World War II and was later modified by Kistler and Nitschmann and other scientists (14, 15). It is generally applied to large (e.g. 4000 L) volumes of thawing plasma to generate a cryoprecipitate which contains part of the fibrinogen as well as much of the Factor VIII and associated vWF. The supernatant is then subjected to a complex series of cold temperature precipitation steps in the presence of ethanol with various shifts of pH, temperature and conductivity (FIG. 1, redrawn from Ref 16). In modern plasma fractionation processes (e.g. FIGS. 2A and 2B, from Ref 15) these different precipitation steps yield fractions which are then subjected to further purification using chromatographic processes. In general the advantages of Cohn Fractionation include the fact that it can be applied to large volumes of plasma; that plasma protein fractions end up as precipitates which can be intermittently stored as needed; that some fibrinogen is removed early in the process so that it does not foul chromatography columns in follow-on separation steps; the ability of the processes to inactivate some bacteria, virus and perhaps prions; the ability of the process to be matched with solvent-detergent (SD) or related antiviral methods. Disadvantages include: a. The need to use large and fairly concentrated amounts of ethanol which presents both health and explosion/fire hazards leading to expensive processing equipment and facilities. b. The need for fine-tuned (+/−3° C.) temperature control which in the case of large liquid volumes further complicates processes and related equipment and facilities. c. Unit operations involving high concentrations of ethanol (up to 40%) and low pH as well as relatively long processing times which can denature some target proteins. d. Proteins such as fibrinogen and immunoglobulins have to be (partially) recovered as precipitates at different stages (e.g. FIGS. 2A and 2B). e. Protein recoveries can be quite poor e.g. 50% for immunoglobulins in some processes (above references). The alternative of using salt precipitation for fractionation (22) leads to very high salt contents in the recovered protein fractions, necessitating costly additional operations like dilution or diafiltration before further processing of these fractions. It may also lead to denaturation of the proteins. Fractionation using precipitation with non-ionic polyethylene glycol (PEG) and sodium chloride has also been attempted (23), but this requires very high concentrations of PEG and corrosive sodium chloride. In addition, this process is very pH-sensitive and careful adjustment of pH and conductivity is needed after each precipitant addition. It also needs complex additional processing to remove PEG from the proteins.

Given the above there is a need to identify simpler, robust and easily scaled alternatives to centrifuge-based blood cell isolation from plasma. There is also a need to identify simpler, easily scalable alternatives to Cohn Fractionation (14,15). It should also be noted that there is a need to identify rapid and simple methods to isolate plasma proteins for diagnostic and research purposes.

SUMMARY OF THE INVENTION

One aspect of the present invention relates to a method of selectively separating proteins from plasma, isolated from blood. This is achieved with a process according to claim 1. The method can be employed in a selective manner to separate specific abundant proteins such as fibrinogen, immunoglobulins and albumin. Selectivity and protein recovery can be further controlled via use of pH, and salt composition. The method is also robust in regard to delivering similar separations in the face of normally expected process variations (i.e. +/−10% of stated operational values) in polymer type, polymer concentration, temperature, pH etc. and complex adjustments of buffer pH, conductivity etc. between the precipitation steps are not needed. It is also robust to protein concentration, such that it can be used at different stages of plasma processing which involve protein concentrations above the plasma levels. In contrast to prior plasma fractionation methods it can even be used directly on undiluted plasma, which allows for significant cost reductions.

A second aspect of the present invention also relates to a process of spontaneously isolating plasma proteins from blood cells and blood lipid components. This is achieved by a process according to claim 33. The process can be used alone or as a step together with the method of the first aspect in a plasma separation process. Advantages of the invention include that: a. It requires little or no energy to affect the separation other than mixing, b. It can be performed in variety of containers including disposable single use plastic containers, c. It employs relatively inexpensive and biocompatible reagents, d. It functions over broad ranges of scales and temperatures, e. It leaves the bulk of proteins in an aqueous phase which is amenable to be directly used in further target processing including via depth filtration (to remove any cellular, cell debris, bacterial, or other colloid contaminants) and then further purification of proteins by precipitation, chromatography, etc.

The above two methods can be employed together or individually to effect clarification and selective precipitation of proteins in regard to processing of blood and plasma.

Further suitable embodiments of the invention are described in the depending claims.

REFERENCES

1. D J Roush, Y Lu, Biotechnol Progr 24, 488-495, 2008
2. J Thommes, M Etzel, Biotechnol. Progr. 2007, 23, 42-45.
3. A M Azevedo et al Trends in Biotechnology, 27, 240-247, 2009.
4. WO 2010/080062
5. H-O Johansson, et al. J. Chromatogr B, 711, 3-17, 1998.
6. H-O Johansson, et al. Biotechnol Bioeng, 66, 247-257, 1999.
7. WO 2010/082894
8. WO 2008/091740.
9. P McDonald, et al Biotechnol Bioeng, 102, 1141-1151, 2009.
10. P Thanmaya, et al, Biotechnol Progr, 28, 1322-1331, 2010.
11. A Venkiteshwaran et al, Biotechnol Bioeng. 101, 957-966, 2008.
12. WO 2008/100578
13. U.S. Pat. No. 3,974,134
14. A Lihme et al, Anal Biochem, 399, 102-109, 2010.
15. T Burnouf. Transfusion Medicine Reviews, 21, 101-117, 2007.
16. E. J. Cohn et al, J. Am Chem. Soc, 68, 459-475, 1946.
17. L Jiang et al, J Chromatogr A, 1023, 317-320, 2004.
18. J Ma et al. J. Chromatogr B, 862, 219-226, 2008.
19. Odile Caretter et al. Nature Protocols. 1, 812-823, 2006.
20. F. Carlsson et al, J. Phys. Chem. B. 105, 9040-9049, 2001.
21. A. Witteman et al, Progr. Colloid Polym. Sci. 133, 58-64, 2006.
22. U.S. Pat. No. 7,879,332
23. Y-Z Lee et al, J. Agr. Food Chem. 35, 958-962, 1987

DEFINITIONS

Figure 1:
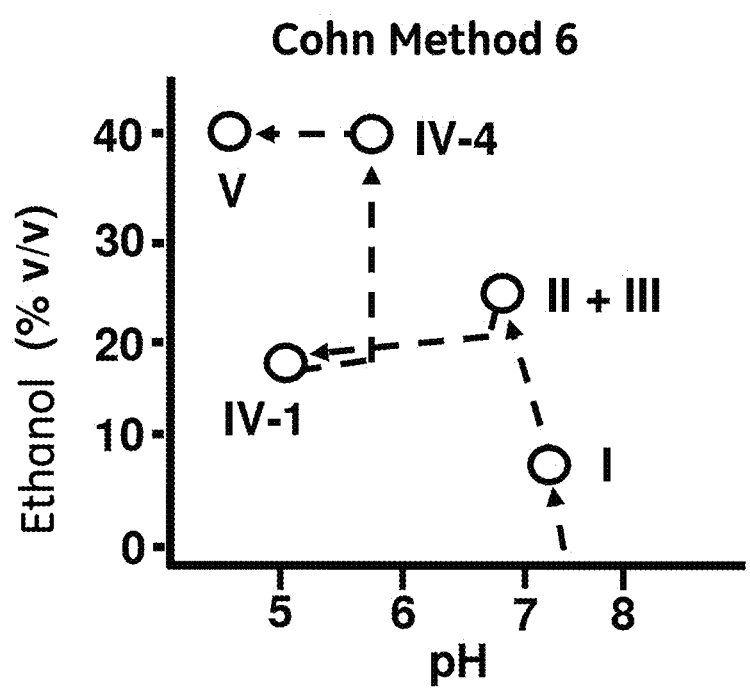
FIG. 1. Diagram showing complexity of Cohn Fractionation Process 6 from 1946 in terms of variation in pH and ethanol concentration redrawn from Cohn et al., reference 16.

The term "polyacid" herein means a polymer comprising functional groups that are negatively charged at pH 6 and higher.

The term "self-associating responsive polymer" herein means a water soluble polymer comprising hydrophobic segments and exhibiting a cloudpoint, i.e. a temperature above which an aqueous solution of the polymer segregates into two phases.

DETAILED DESCRIPTION OF THE INVENTION

In one aspect the present invention discloses a process for separating at least a first and a second protein from a sample of blood plasma, comprising the steps of:
a) providing a sample of blood plasma in a container,
b) adding a polyelectrolyte such as a polyacid and a salt to the blood plasma, leading to formation of a first protein precipitate and recovering the first protein precipitate and a first supernatant,
c) adding polyelectrolyte/polyacid and/or a salt to said first supernatant, causing formation of a second protein precipitate and a second supernatant and recovering the second protein precipitate separately,
wherein the first protein precipitate comprises a concentrate of the first protein and the second protein precipitate comprises a concentrate of the second protein.

By concentrate is meant that the mass ratio of the protein in question (first or second protein) to the total protein amount in the protein precipitate is significantly higher than said mass ratio in the blood plasma or in the first supernatant. It can e.g. be at least twice as high, at least ten times as high or at least fifty times as high. This can also be expressed in terms of the first and second proteins being enriched in the respective protein precipitates. Further, the first protein precipitate may comprise at least 50 wt %, such as at least 70 wt % or at least 90 wt % of the total amount of the first protein in the blood plasma sample and the second protein precipitate may comprise at least 50 wt %, such as at least 70 wt % or at least 90 wt % of the total amount of the second protein in the first supernatant or in the blood plasma sample. The blood plasma sample used can be a non-diluted plasma.

The method selectively concentrates and isolates proteins from plasma, isolated from blood by standard methods such as centrifugation and filtration or partition methods, via addition of a polyacid. The method can be employed together with a salt, including citrate anticoagulant, to non-specifically precipitate most of the plasma protein. It can also be used in selective manner to separate specific abundant proteins such as fibrinogen with the supernatant then being exposed to a higher polymer concentration to fractionally precipitate immunoglobulin. The supernatant from separation can then be exposed to yet higher polymer and/or salt concentrations, to isolate other remaining proteins from serum albumin. Plasma contains a large number of proteins—about a hundred in addition to the most abundant proteins (Table 1) and gel electrophoresis suggests that the above precipitant fractions will contain other proteins which may also be of commercial, diagnostic or research interest. Selectivity and protein recovery can be further controlled via use of pH, and salt composition. However the method is very robust in regard to effects of normal process variations (i.e. +/−10% of stated operational values) in polymer type, polymer concentration, temperature, pH etc. It can be operated at temperatures from 0 to 40° C., such as from 4 to 20° C. in either one or both of steps b) and c). The method can also be combined with a pathogen inactivation or removal step, such as a solvent-detergent step, a virus filtration step and/or a low pH virus inactivation step. The blood plasma may be human, but it could also be of animal origin, e.g. bovine or equine blood plasma.

Advantages of the Polyacid Precipitation Approach are that:
I. It does not require any organic solvent.
II. It can be performed in variety of containers including disposable single use plastic containers.
III. It employs benign and inexpensive reagents.
IV. It is expected to isolate nucleic acid and some other contaminants into the supernatant.
V. It can be performed over a wide range of temperature.
VI. It results in defined, stable and easily handled precipitates which are also easy to re-dissolve in variety of solutions for further processing.
VII. It is amenable to processing of plasma protein samples from small (microliter) to large (thousand liter) scales.
VIII. It is amenable to processing not only human plasma proteins but also proteins in mixtures from other sources (e.g. bovine plasma).

Figure 2A:
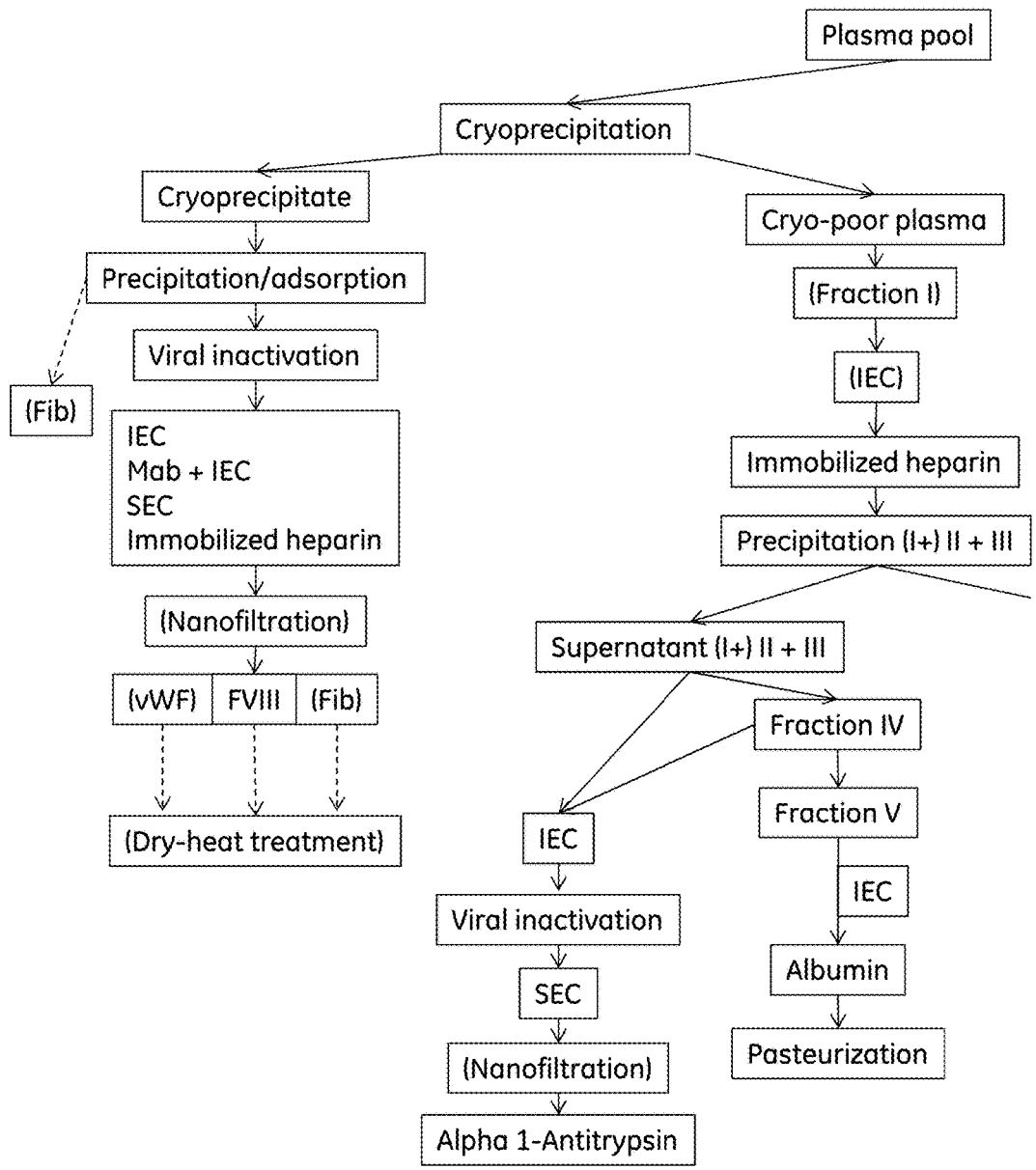
FIGS. 2 A and B. Split diagram showing complexity of modern Cohn-based precipitation and related chromatographic plasma fractionation processes taken from Burnouf, reference 15.
Figure 2B:
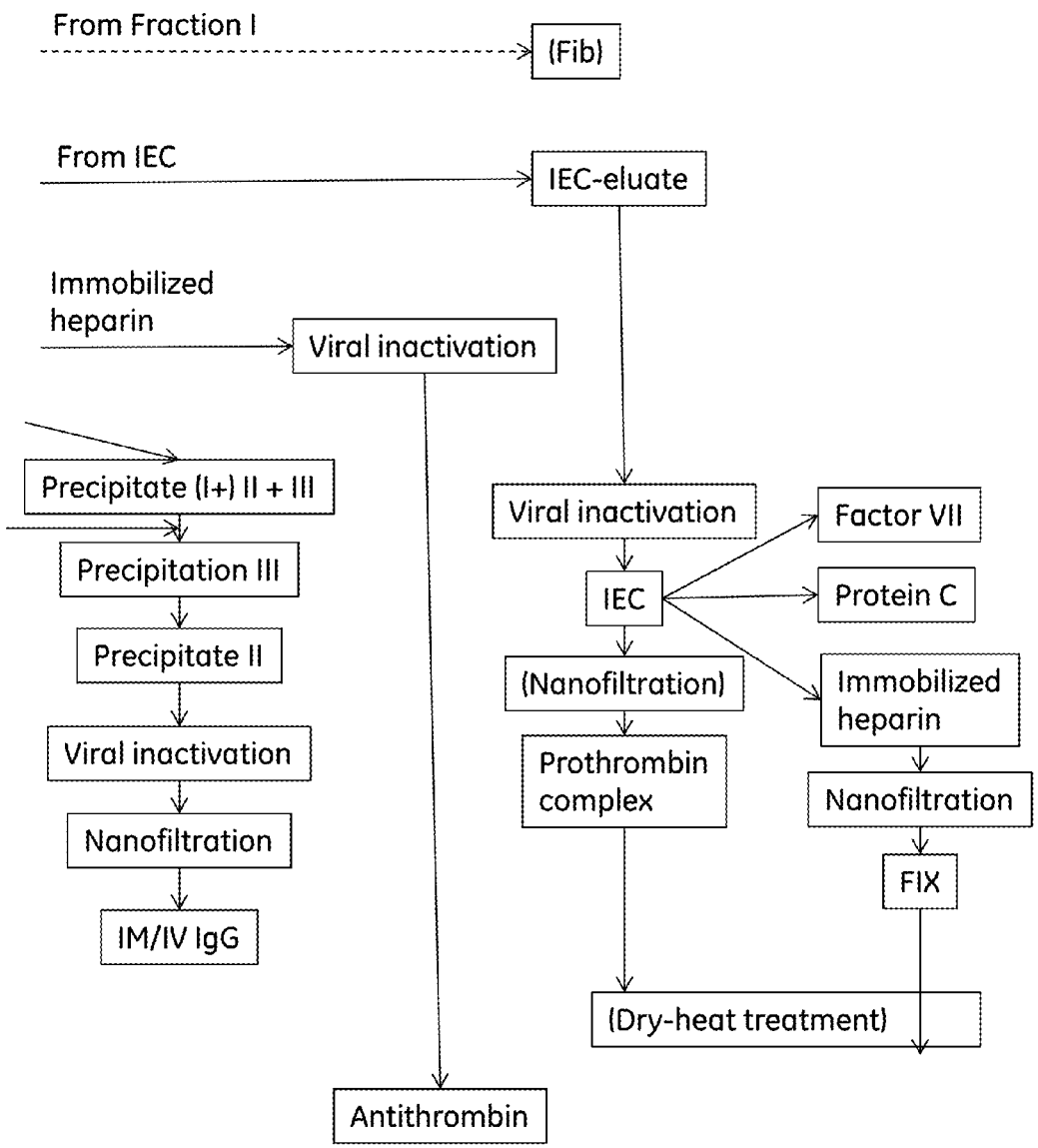
Figure 3:
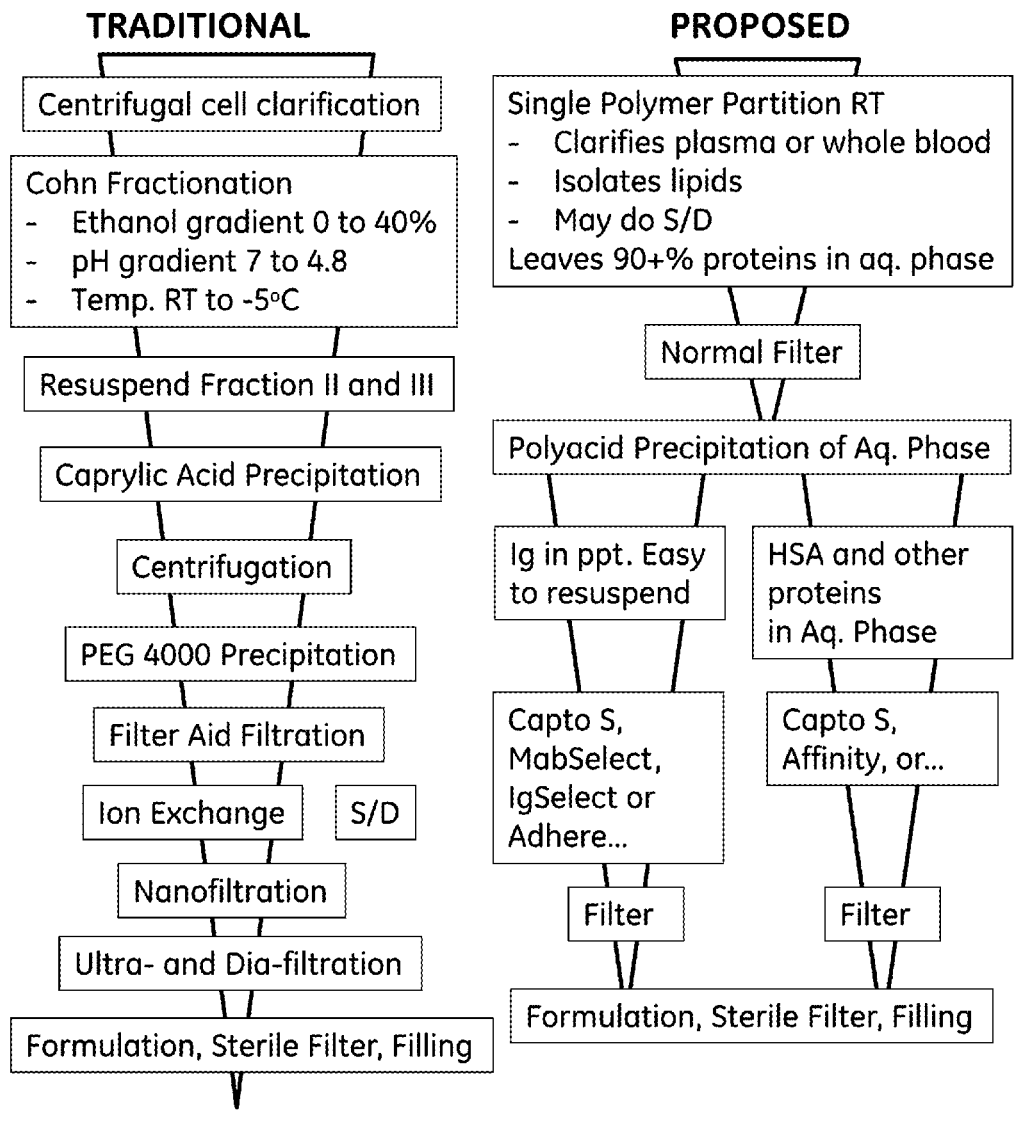
FIG. 3. Simplified overview of Cohn-based precipitation and related chromatographic plasma fractionation processes of cell-free plasma sample, compared to a process of the invention based on single polymer phase system for bulk removal of cells prior to polyacid based precipitation. In the both cases fibrinogen is removed in the first precipitation steps (not shown).

The basic advantages of the combined approach are shown in FIG. 3 which provides a simplified description of a standard Cohn-based plasma protein fractionation process (shown in more detail in FIGS. 1 and 2) compared to a process where cells may be isolated via partitioning (or in classical centrifugal approach) followed by polyacid based precipitation. The polyacid precipitation approach appears to satisfy all of the needs for a method to replace Cohn Fractionation as summarised below. The advantages of the combined partition and precipitation approach are summarised in Table 2. Other features of the above will be apparent from the following detailed examples and from the claims.

Needs for a Cohn Fractionation Replacement Method:

1. Have comparability to Cohn Fractionation so as to be readily applied to existing facilities and processes. For example it should isolate fibrinogen, immunoglobulin and albumin proteins in separate fractions, and be capable of isolating such proteins in (easily re-dissolved) precipitant complexes which may also provide stable short term storage.

2. Involve little or no organic solvents so as to reduce health, safety and cost issues; as well as provide for processing in simpler facilities.

3. Be amenable to processing at uniform temperature from 4° C. to room temperature (e.g. 20° C.) so that complex control systems for varied temperature are not needed.

4. Offer as good or better yield of proteins such as immunoglobulin.

5. Remove most fibrinogen early in process so as to promote efficient follow-on purification via chromatographic or other porous media based steps.

6. Be possible to operate without significant alteration in working solution composition as compared to the complicated pH, conductivity and solvent composition variations of Cohn Fractionation (FIG. 1).

7. Involve fewer precipitation steps than Cohn Fractionation and not involve steps which require other precipitants such as polyethylene glycol (FIG. 2A). For example sequential addition of single precipitant, at single temperature, and relatively low concentration (compared to the 20 to 40% ethanol levels of Cohn Fractionation (16)).

8. Be cost effective in terms of utilising relatively low concentrations of biocompatible reagents which may be readily removed via follow-on chromatography steps.

9. Be readily implemented using sterile plastic bags and other disposable equipment so as to allow for flexible manufacturing, and easy set-up of new facilities.

10. Involve liquid process streams and robust methods so as to readily allow for easy integration of low pH steps, solvent-detergent steps, and filtration steps to aid removal of pathogenic contaminants such as bacteria, virus, prions and related substances. This is in addition to any removal afforded by full process associated chromatographic steps.

11. Offer significant reduction (10-100×) of nucleic acid and other contaminants in addition to any removal afforded by full process associated chromatographic steps.

12. Be amenable to addition of stabilizers, anti-aggregation agents, anti-proteolytic agents if required to promote recovery of active protein target in native functioning state.

TABLE 2

Summary of Cohn and New Polymer Based Plasma Fractionation Processes.

| Attribute | Classic Fractionation | New Polyacid Fractionation |
|---|---|---|
| Cell Removal | Centrifuge or Filter | Partition or Classic Methods |
| Starting State | Thawed (Prev. Frozen) Plasma | Fresh or Thawed Plasma |
| Anticoagulant | Citrated or otherwise treated | Citrated (other not tested) |
| Plasma Sample Dilution | Often 2-3x | 3x, or less |
| Clarification | Centrifugation Plus Filtration | Centrifugation (or EOPO Partition) Plus Filtration |
| Polymer for Precipitation | Often polyethylene glycol [i.e. poly(EO)] to aid precipitation | Polyacrylic or other polyacid |
| Caprylic Acid | Often Used | Not needed |
| Solvent Type | Ethanol at high concentration | No Solvent |
| Solvent Issues | Flammable/Inhalation/Explosion | No Solvent |
| Temp. Control | May require varied temperature | Isothermal 4° C. or RT |
| Precipitation Selectivity | Temp., pH, Ethanol gradients | Polyacid, pH or salt |
| Antiviral Solvent/Detergent (S/D) or pH 4 treatment | Separate Step | May be built into process. See FIG. 3. |
| Major Protein Recovery | Fibrinogen → Ig → Albumin | Fibrinogen → Ig → Albumin |
| Other Protein Fractions | Possible | Possible |
| Fractionation Steps | Many (i.e., 5 in FIG. 1) | Fewer (i.e., 3) |
| Easily resuspended ppt. | May require significant dilution | Simple 1:1 dilution |
| Pre-Chromatography | Suspension, Desalt, Filtration | Filtration |
| Chromatography | Depends on pre-treatment | All Types |

In some embodiments the first protein can be fibrinogen. The second protein can be an immunoglobulin, such as immunoglobulin G. Fibrinogen typically precipitates at lower polyacid concentrations than immunoglobulins and it is an advantage of the method that the precipitation selectivity is similar to what is observed in the Cohn fractionation. This reduces fouling or other process complications related to fibrinogen. Fibrinogen and immunoglobulin G are both valuable proteins and commonly used as pharmaceuticals. In some embodiments the first and second proteins are suitable for use as pharmaceuticals, meaning that they (optionally after further separation steps) have sufficient purity for pharmaceutical use and are devoid of toxic contaminants introduced by the process. In certain embodiments a sufficient amount of polyacid is added in step b) or c) so that the second protein precipitate comprises essentially all the remaining proteins from the blood plasma. This precipitate can then be processed further for separate recovery or analysis of a multitude of proteins.

In certain embodiments, the salt addition in step b) is controlled such that in step b) the blood plasma comprises at least 50 mmol/l, such as 50-250 mmol/L, or 50-100 mmol/L, of the salt, calculated on the anion of the salt. It can also be controlled such that the total salt concentration in step b) is at least 50 mmol/l, such as 50-250 mmol/L, or 50-100 mmol/L, again calculated on the anion. The polyacid and the salt show a strong cooperative effect, meaning that relatively low salt concentrations can be used to obtain an efficient fractionation. This is advantageous, as low salt concentrations in the precipitate allow for direct processing of redissolved precipitate by methods such as cation exchange chromatography without excessive dilution or diafiltration. If chloride salts are used, a further advantage of working at low salt concentrations is that corrosion of stainless steel equipment is diminished. The salt can be added either as an aqueous solution or as a solid powder.

In some embodiments the polyacid in step b) is added in an amount to give a total polyacid concentration in the blood plasma of at least 3 wt %, such as 4-10 wt % or 4-5 wt %. The exact concentration to be used depends to some extent on the salt concentration and some limited experimentation will be needed to determine which concentration to use for a particular separation task. The polyacid can conveniently be added in the form of an aqueous solution, if desired also as a mixed polyacid-salt solution. Optimization can be carried out using pure proteins or via experiments run with simple electrophoretic analysis per e.g. the cubic centered face design (CCF) of experiments, as shown in FIGS. 8, 9, 15, 16.

In certain embodiments the polyacid in step c) is added in an amount to give a total polyacid concentration in said first supernatant which is equal to or higher than the polyacid concentration in step b) and is at least 4 wt %, such as between 5 and 20 wt %, between 5 and 15 wt % or between 5 and 8 wt %. If the salt concentration in step c) is the same as in step b), a higher polyacid concentration will be needed in step c) than in step b), while if further salt is added in step c), the polyacid concentration can be either equal to or higher than in step b). In certain embodiments, in particular when the polyacid concentration is about 15-20%, the second protein precipitate in step c) can be recovered as a floating or top phase.

In some embodiments the salt addition in step c) is controlled such that in step c) the first supernatant comprises at least 50 mmol/L such as 50-250 mmol/L or 50-100 mmol/L, of the salt calculated on the anion of the salt. It can also be controlled such that the total salt concentration in step c) is at least 50 mmol/l, such as 50-250 mmol/L, or 50-100 mmol/L. The salt concentration in step c) can be equal to the concentration in step b) (no salt added in step c)) or it can be higher than in step b) if further salt is added. It is again an advantage that the total salt concentration can be kept at a low level to facilitate further downstream processing of the precipitate and to minimize corrosion.

In certain embodiments said polyacid is selected from the group consisting of polyacrylic acid (PAA), polymethacrylic acid (PMAA), polyvinylsulfonic acid (PVS), polystyrenesulfonic acid (PSS), carboxymethyl dextran (CMD) and carboxymethyl cellulose (CMC). These polymers are commercially available and can be produced to adequate purity and with suitable molecular weights. In general terms, the polyacid can be a polymer that comprises e.g. carboxylate, sulphonate and/or sulphate groups, which are all negatively charged at pH above about 5 and the content of these groups can be about 2-15 mmol/g polymer (e.g. 5-15 mmol/g), as calculated from the acid form of the polymer (PAA 14 mmol/g, PMAA 12 mmol/g, PVS 9 mmol/g, PSS 5 mmol/g, CMD and CMC depending on degree of substitution). The molecular weight of the polyacid can be at least 5 000 Da, such as 5 000 to 40 000 Da or 5 000 to 15 000 Da. Lower molecular weights may give less robust precipitation, while too high molecular weights result in solutions with high viscosities.

In some embodiments the salt added in step b) (and optionally in step c)) is selected from the group consisting of sodium phosphates, potassium phosphates, ammonium phosphates, sodium citrates, potassium citrates, ammonium citrates, sodium sulphates, potassium sulphates, ammonium sulphates, sodium acetate, potassium acetate, ammonium acetate or any combination thereof. Several of these salts have multivalent anions and both monobasic, dibasic, tribasic and mixed salts of these anions can be used depending on the pH of the system. It is to be understood that adding a mixed solution of an acid corresponding to the anion of a salt and a sodium, potassium or ammonium hydroxide is equal to adding the salt as such. In general terms the salts can be chosen from lyotropic salts giving a high salting-out effect according to the well-known Hofmeister series and which do not give toxicity or other negative effects. Sodium phosphates and sodium citrates are advantageous, as they are often used in plasma processing where they offer pH buffering and anticoagulation properties. Salts can be used alone as per FIG. 1 or in combinations. This includes combinations with other salts, such as e.g. sodium chloride as per FIGS. 15 and 16. Salt concentrations exceeding the solubility product of any applied salt under the conditions used can advantageously be avoided.

In certain embodiments in steps b) and/or c) the pH is between 4 and 9, such as between 6 and 8. The pH can be kept constant throughout the fractionation or it can be optimised for each precipitation step. In some embodiments, no pH adjustment is made between the precipitation steps. The process is relatively robust to normal process pH variations (e.g. +/−0.2) within these intervals, but pH can be used to fine tune the selectivities of the precipitation steps.

In some embodiments step c) further comprises recovering a second supernatant and further comprising a step d) of adding polyacid and/or a salt to said second supernatant, causing precipitation of a third protein precipitate comprising a concentrate of a third protein and recovering this third protein precipitate. This third protein can be an albumin, such as human serum albumin, but it can also be a less abundant protein, e.g. Factor VIII or transferrin. By concentrate is meant that the mass ratio of the third protein to the total protein amount in the protein precipitate is significantly higher than said mass ratio in the blood plasma or in the second supernatant. It can e.g. be at least twice as high, at least ten times as high or at least fifty times as high. This can also be expressed in terms of the third protein being enriched in the third protein precipitate. Further, the third protein precipitate may comprise at least 50 wt %, such as at least 70 wt % or at least 90 wt % of the total amount of the third protein in the blood plasma sample or in the second supernatant.

The precipitate(s) may include more than one target protein, requiring further processing of the mixture(s). In certain embodiments at least one protein precipitate, such as each protein precipitate, is redissolved and subjected to a further step such as precipitation, crystallisation, chromatography, and/or filtration for separation of said first, second and/or third protein. Due to the relatively low salt contents in the redissolved precipitates, ion exchange chromatography is an attractive method for a following step. Both cation exchange and anion exchange chromatography, as well as multimodal ion exchange chromatography, can be used directly with the redissolved precipitate. Residual amounts of polyacid present in the precipitates may be removed by a flowthrough anion exchange chromatography step. It is also possible to use bind-elute chromatography, e.g. via hydrophobic interaction, affinity, mixed mode or cation exchange chromatography.

In some embodiments step a) is preceded by a step a') of separating blood cells from blood by aqueous two-phase separation. Step a') may in turn comprise the substeps of:
i) adding a self-associating responsive polymer, and optionally a salt, to a sample of blood,
ii) increasing the temperature or adding salt, causing the formation of a polymer rich aqueous phase, a polymer poor aqueous phase and a phase interface comprising blood cells and
iii) recovering the polymer poor aqueous phase as the blood plasma.

This step is useful to provide a cell-free blood plasma, but also to recover blood cells and lipids from the blood.

In some embodiments the total responsive polymer content in step ii) constitutes about 4-20 wt % of the total system.

In certain embodiments pH in step ii) is between 6 and 8, such as between 7.3 and 7.5.

In some embodiments the concentration of added salt in step ii) is in the range of 1-500 mmol/L, such as in the range of 100-300 mmol/L. The salt in this step may be selected from the group consisting of sodium chloride, sodium phosphates, potassium phosphates, sodium sulphate, potassium citrates, sodium citrates, ammonium sulphate and sodium acetate; or any combination thereof.

In certain embodiments in substep i) or ii) 1-10 wt % ethanol is added to the blood. This may enhance the phase formation, particularly the formation of a lipid-rich phase.

In some embodiments the self-associating responsive polymer exhibits a cloud point in 1% aqueous solution between 2 and 100° C., such as between 2 and 40° C. The polymer can comprise poly- or oligoethylene glycol segments and can be selected from the group consisting of ethylene oxide-propylene oxide copolymers and ethylhydroxyethylcellulose. One example of such polymers is ethylene oxide-propylene oxide random copolymers available under the name of Breox from Cognis, Germany and under the name of Ucon from Dow, USA. Another example is ethylene oxide-propylene oxide block copolymers available under the name of Pluronic from BASF, Germany and Tergitol L from Dow, USA. Yet another example is ethylhydroxyethylcellulose available as Bermocoll from Akzo Nobel Cellulosic Specialties, Sweden. The self-associating responsive polymer can have a molecular weight in the range of 900-100 000 Da.

In some embodiments a second polymer, such as dextran, polyacrylic acid, starch or a starch derivative may be used in conjunction with the self-associating responsive polymer to form a two-polymer aqueous phase system.

In certain embodiments step a') is run in a continuous mode, e.g. by the application of a decanter centrifuge or a continuous gravity settler to separate the phases.

In some embodiments one or more of the sequential precipitation steps b)-d) and/or the aqueous two-phase separation step a') is performed in one or more flexible single use containers such as one or more flexible plastic bags. The steps are well adapted to such containers in that they do not involve volatile and flammable solvents and this is a highly useful feature in that it reduces the need for costly cleaning validation and for investment in heavy stainless steel equipment. Necessary agitation for precipitation and/or aqueous two-phase separation can be supplied by having the flexible plastic bag(s) mounted on a rocking platform or via other mixing solution used with, for example, single use bioreactors.

In certain embodiments the polymer poor aqueous phase of step ii) can be freeze dried or stored at low temperature for at least one day or one week. The storage temperature can be below 8° C. (e.g. 4 8° C.), or below 0° C. (e.g. −10−−20° C. or −50−−80° C.). This means that the process steps can be separated in time, which can be practical in many manufacturing or analysis situations. Residual polymer from the partitioning step can have a cryoprotectant effect, which improves the stability of sensitive proteins during storage.

In some embodiments the polymer poor aqueous phase of step ii) may contain added stabilizers, anti-aggregation agents and/or anti-proteolytic agents if required to promote storage and recovery of active protein target in native functioning state.

In some embodiments step a') is performed in plastic containers, such as flexible plastic bags, microtiter plates etc. The plastic bags may be connected with plastic tubing, forming a disposable set for carrying out the partitioning step. The self-associating responsive polymer, and optionally the salt and any other liquids or reagents may be present in the plastic containers before introduction of the blood in the containers. Such prefilled plastic containers may be supplied in the form of a kit together with written instructions for carrying out the separation.

Of particular interest are also precipitation and partitioning methods for analytical or laboratory scale preparations, which can isolate abundant plasma proteins, which tend to mask analysis of less abundant, but physiologically significant proteins. Such approaches can be run in high throughput mode in microliter volumes on robotic liquid handling stations and do not involve active (energetically driven) separation methods such as chromatography, electrophoresis, or centrifugation. Analytical and lab scale precipitation and/or partitioning will typically be applied to scales <500 ml, such as below 10 ml.

A second aspect of the present invention discloses a process for preparation of blood plasma, comprising the steps of: i) adding a self-associating responsive polymer, and optionally a salt, to a sample of blood,
ii) increasing the temperature or adding salt, causing the formation of a polymer rich aqueous phase, a polymer poor aqueous phase and a phase interface comprising blood cells and
iii) recovering the polymer poor aqueous phase as the blood plasma.

In other words, this is a process of spontaneously isolating plasma proteins from blood cells and blood lipid components via simple addition of thermo-responsive polymer to blood under conditions of temperature where the polymer induces formation of a two-phase system. One phase has a relatively high concentration (i.e., is enriched in) polymer and the other contains much lower concentration of polymer (e.g. 1 wt %) and is rich in water. Proteins predominantly partition to the aqueous phase depleted of cellular and lipid components and containing little polymer (e.g. 1%). If significant lipid is present it may be found in a third phase. In some cases adding a few wt % solvent (e.g. 5-10% ethanol) may help resolve the lipid phase relative to the other phases. Cellular components are to be found at the phase interface where they are held by interfacial tension. The systems can be compounded with presence of NaCitrate at concentrations commensurate with anticoagulation. The approach can be used for isolation of blood proteins (and lipid components) from cellular components for a variety of purposes including large volume plasma protein fractionation, or small volume diagnostic or research purposes. It is particularly useful as a first step in blood plasma processing, followed by at least one step where a water soluble polymer is added to the blood plasma, causing precipitation of at least one protein. This step can e.g. be a polyacid sequential precipitation step according to the first aspect of the invention.

Main Advantages of the Partition Approach are that:
a. It requires little or no energy to affect the separation other than mixing,
b. Can be performed in variety of containers including disposable single use plastic containers,
c. Employs relatively inexpensive and biocompatible reagents,
d. Functions over broad range of scales and temperatures,
e. Leaves bulk of proteins in an aqueous phase which is amenable to other be directly used in further target processing including via depth filtration (to remove any cellular, cell debris, bacterial, or other colloid contaminants) and then further purification of proteins by precipitation, chromatography, etc.

In some embodiments, the polymer poor aqueous phase of step ii) or iii) may be mixed with a self-associating responsive polymer, and optionally a salt, causing a second formation of a polymer rich aqueous phase and a polymer poor aqueous phase. Different target proteins may then be enriched in each phase and recovered for subsequent processing or analysis. Such an operation may also be carried out with recycling of used polymer solutions and can also be carried out in a cascade mode.

EXAMPLES

A. Materials and Methods
Polymers

Figure 8:
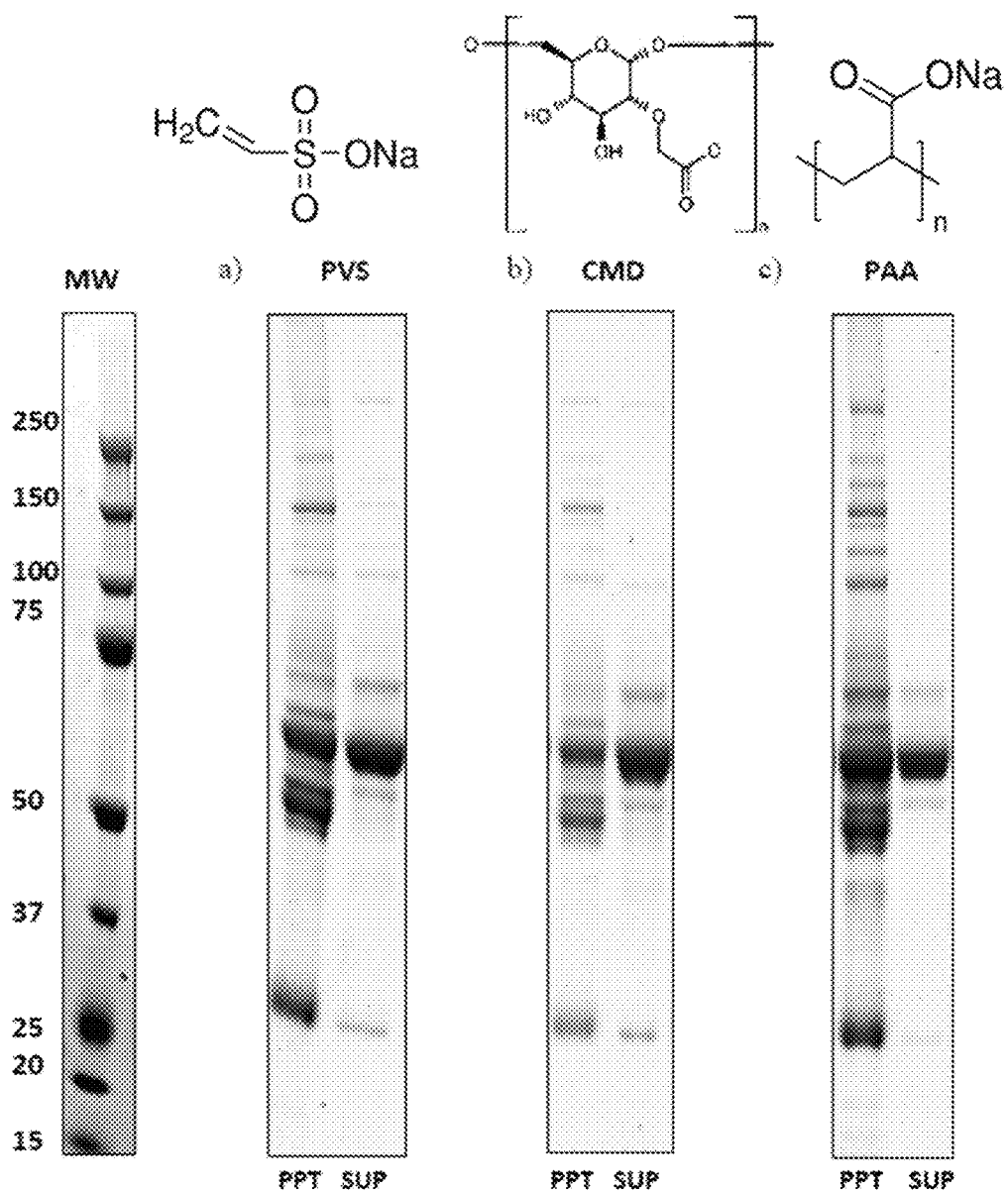
FIG. 8. 1D reduced SDS gel electrophoresis analysis of precipitate and supernatant samples related to polyacid precipitation of plasma proteins in the presence of 200 mM NaCitrate, pH 7. PVS (11% (w/w) polyvinylsulfonic acid 3 000, CMD (20% carboxymethyldextran), PAA (10% polyacrylic acid 15 000) with polymer concentration varied to effect approximately similar concentration of charged groups in solution.

The anionic polymers used in this study were sodium polyacrylic acid (PAA), polyvinylsulfonic acid (PVS) and carboxymethyl dextran (CMD), FIG. 8. Stock solutions of sodium salt of PAA of different molecular weights and stock concentration ($M_w$ 8000, 45% (w/w) and $M_w$ 15000, 35% (w/w), are assumed to have one carboxylate group per monomer of $M_w$ 72), and PVS of $M_w$ 3000, 25% (w/w) (assume one sulphonate group per monomer of $M_w$ 107) were purchased from Sigma-Aldrich (St. Louis, USA). CMD of $M_W$ 40000, degree of substitution (DS) 1.39 was purchased from Meito Sangyo (Japan). Polymers typically exhibit a range of pKa's. The PAA and CMD are expected to have pKa ranges below 5 and PVS below 4 so they are all expected to be highly negatively charged at pH>6. The "EOPO" type copolymer used in this study to aid the ATPS formation is a common industrial surfactant called Breox®. Fairly similar copolymers including Pluronic® block copolymers and Tergitol® random copolymers are available from several sources. Some are used in the food industry or as surfactants in bioprocessing. Breox 50 A 1000 is a random copolymer consisting of 50% ethylene oxide and 50% propylene oxide. Its molecular mass is 3900 and it was obtained from International Specialty Chemicals (Southampton, UK). Breox polymers are now supplied by Cognis in forms suitable for food and other processing. All polymers were used directly from the shipping containers.

Proteins and Plasma

The protein Gammanorm (165 mg/ml) used in this study is a blood derived human polyclonal Ig purchased from Octapharma AB (Stockholm, Sweden), which is referred to as IgG throughout the document. Human serum albumin (HSA) and bovine fibrinogen were purchased from Sigma-Aldrich (St. Louis, USA) and human transferrin was purchased from Kabi (Uppsala, Sweden). The mAb (20.7 mg/ml) used in the study was obtained internally (GE Healthcare, Uppsala, Sweden) and produced in Chinese Hamster Ovary (CHO) cells (mAb2, 20 mM citrate pH 7, filtered 0.22 µm). Plasma purchased from the Blood Central in Uppsala, was obtained from plasmaphoresis and freshly frozen. It was not defatted or otherwise treated prior to experimentation.

Buffers, Salts and Other Solutions

When examining the partitioning of plasma proteins in an aqueous two-phase system (ATPS) based on EOPO polymer and the precipitation of plasma proteins with PAA the following buffers were used:

NaCitrate 0.8M, pH 3, 5, 7, 9; NaPhosphate 0.8M pH 7; NaCl 5M

In the HiTrap™ Q Sepharose™ Fast Flow analysis the following buffers were used; Buffert A 50 mM NaCitrate, pH 4.5; Buffert B 50 mM NaCitrate pH 4.5+1M NaCl Cleaning in Place (CIP) 1M NaOH (Merck, Darmstadt, Germany); Storage: 20% (v/v) ethanol. NaCitrate buffers of varying concentrations and pH were prepared by mixing appropriate amounts of $Na_3Citrate \times 2H_2O$ (Merck, Darmstadt, Germany) and Citric acid (Merck, Darmstadt, Germany) in MilliQ water (prepared using Millipore water purification apparatus). The NaPhosphate buffers used were prepared by mixing appropriate amounts of $NaH_2PO_4$ (Merck, Darmstadt, Germany) and $Na_2HPO_4 \times 2H_2O$ (Merck, Darmstadt, Germany) in MilliQ water. The 5M Sodium Chloride solution was prepared by dissolving 14.6 g NaCl (VWR, Leuven, Belgium) in 50 ml MilliQ water.

The Biuret solution used in the Biuret assay was prepared as follows:

3.0 g $CuSO_4 \times 5 H_2O$, 9 g $C_4H_4KNaO_6 \times 4 H_2O$, 5.0 g KI was dissolved in 800 ml MilliQ water. 100 ml NaOH (6M) was added and the volume adjusted to 1000 ml with MilliQ water. All chemicals were purchased from Merck (Darmstadt, Germany).

In the Biacore analysis HBS-EP+ (10×) (GE Healthcare, Uppsala, Sweden) was used as buffer. It contains 10 mM hepes (pH 7.4), 150 mM NaCl, 0.5 mM EDTA and 0.5% surfactant P20 and was diluted 10 times in MilliQ water.

Aqueous Two-Phase Systems (ATPS)

To evaluate the possibility to obtain partitioning of plasma proteins with aqueous two-phase systems (ATPS) as seen for mAbs, ATPS based on EOPO polymer and purified plasma proteins were prepared in 10 ml Sarstedt tubes (Sarstedt, Nümbrecht, Germany). The following protein solutions were first prepared in 10 ml Sarstedt tubes:

Gammanorm (5 mg/ml): 0.15 ml Gammanorm (165 mg/ml) was dissolved in 5 ml MilliQ water.

Human serum albumin (HSA) (5 mg/ml): 25 mg HSA was dissolved in 5 ml MilliQ water and subsequently filtered with 0.45 nm sterile filter (Sarstedt, Nümbrecht, Germany).

Fibrinogen (2 mg/ml): 10 mg fibrinogen was dissolved in a 5 ml aqueous solution containing 150 mM NaCl and 100 mM NaCitrate, 100 mM NaPhosphate or 250 mM NaCitrate depending on the system to be studied (3.1), MilliQ water and subsequently filtered with 0.45 nm sterile filter (Sarstedt).

Appropriate volumes of NaCitrate or NaPhosphate buffer of appropriate pH, sodium chloride, protein and polymer were mixed to a final volume of 5 ml in a 10 ml Sarstedt tube to reach desired concentrations. For each ATPS protein system a control sample with the same buffer, salt and protein concentration but no polymer was prepared to be used as a reference in the mass balance calculations. Furthermore a sample containing all except for the protein was prepared for each ATPS system to be used as a blank in the spectrophotometer analysis. The systems were mixed and subsequently left for phase formation at room temperature or at 40° C. in a water bath depending on the system to be examined. ATPS formation at 4° C. was also examined but as expected given the cloud point (Tc) of approximately 40-50° C. for the polymers used no phase formation was observed. It may be possible to effect phase formation at 4° C. using another type of EOPO polymer. Following phase formation 0.1 ml of sample from each phase was diluted in 0.4 ml MilliQ water to be used in the SDS-PAGE analysis.

Polymer Precipitation of Plasma Proteins

PAA was applied directly to the plasma to examine the possibility to selectively precipitate and henceforth isolate valuable therapeutic plasma proteins from the complex mixture of proteins in plasma. The use of other anionic polymers in fractionation of plasma proteins were also investigated such as, PVS and CMD.

Appropriate volumes of plasma, plus the polymer to be examined, and the preferred buffer of desired pH (above) and sodium chloride were added to 10 ml Sarstedt tubes and vortexed for approximately one minute. The mixtures were subsequently left for 15 minutes at room temperature to allow precipitation. The precipitate was pelleted down and harvested by centrifugation at 4000 or lower rpm (see below) for 10 minutes or shorter time (see results) at room temperature (Eppendorf 5810 R centrifuge). The supernatant was isolated from the precipitate and transferred to a new 10 ml Sarstedt tube. The precipitate was resuspended in appropriate volumes of MilliQ water and sodium chloride when needed. 40 µl of sample from the supernatant and the precipitate were diluted in 960 µl MilliQ water to be used in the SDS-PAGE analysis.

Spectrophotometry

Following phase formation in ATPS with EOPO polymer 0.1 ml of sample from each phase was extracted and diluted in 0.9 ml MilliQ water in 2 ml microtubes (Axygen Scientific, California, US). The tubes were vortexed and the solution transferred to 1.5 ml cuvettes (Plastibrand, Sigma-Aldrich, St. Louis, USA). The partitioning of purified plasma proteins between the two phases was monitored spectrophotometrically at 280 nm (Thermo Spectronic UV1, Thermo Fisher Scientific, Walthman, Mass., USA).

The partition coefficient (G), Equation [1], was calculated for each system as well as the percent concentration of each protein in the water phase (C/o), Equation (2). The recovery of each protein was calculated with aid of the reference samples (% recovery), Equation (3).

$$G = \frac{A_{280w} \times \text{phase volume}}{A_{280p} \times \text{phase volume}} \quad (1)$$

$$C/o = \left(\frac{G}{G+1}\right) \times 100 \quad (2)$$

$$\% \text{ recovery} = \frac{(A_{280w} \times \text{phase volume}) + (A_{280p} \times \text{phase volume})}{A_{280ref}} \quad (3)$$

The error estimate for this analysis is approximately ±5% which is why the G values listed below in may differ in the range of 12-15 for HSA, 171-209 for HSA, and 18-22 for IgG. Issues with dissolving pure fibrinogen also contributed to possible error in absolute G value estimates. However the values given below are believed to be indicative and it should be remembered that G values in excess of 10 (e.g. 90% protein in one phase) generally become more inaccurate as G value increases.

Figure 4:
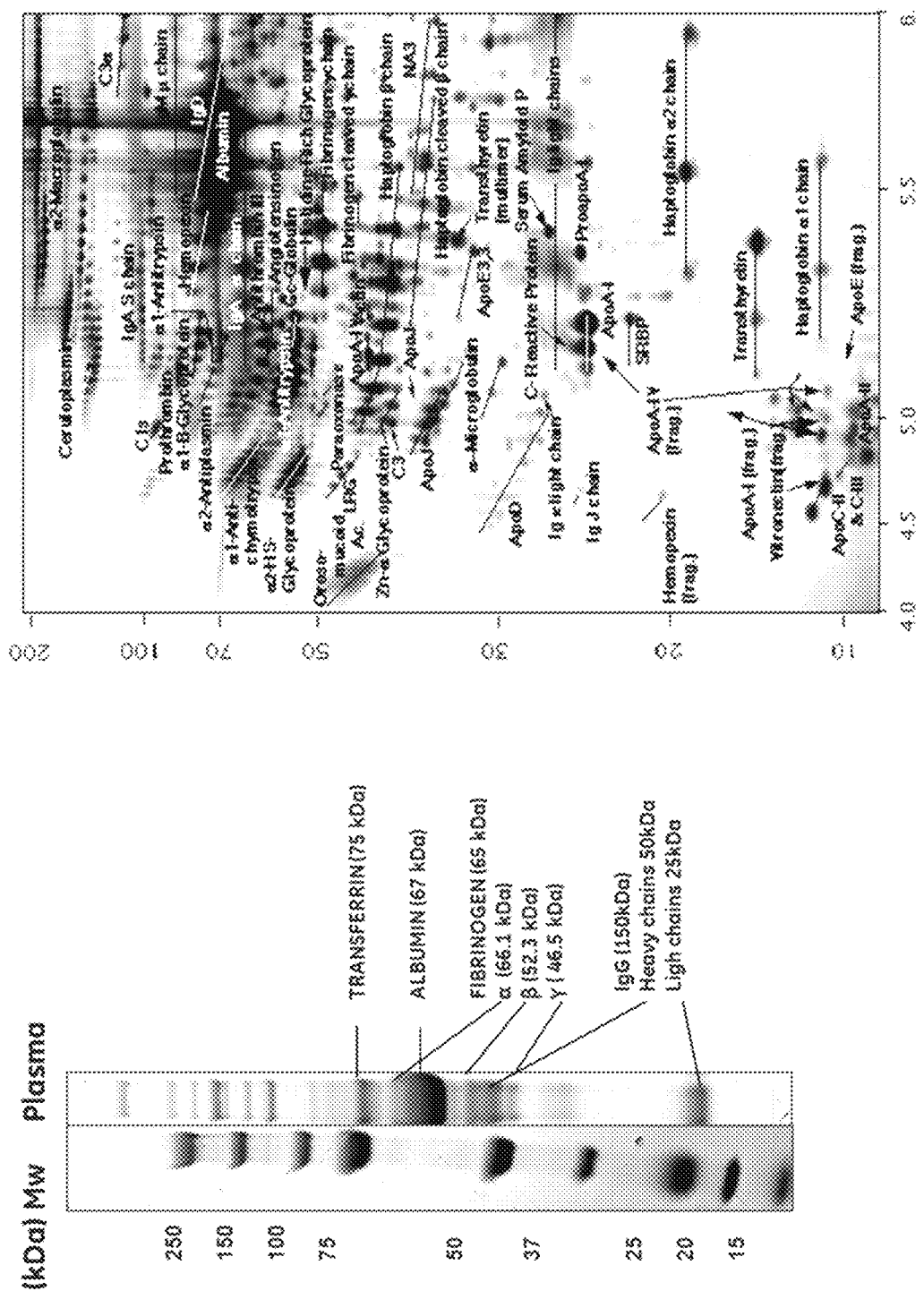
FIG. 4. One dimensional (1D) sodium dodecyl sulphate (SDS) reduced gel electrophoresis analysis of normal human plasma and protein MW standards (from the present work) showing some common bands related to abundant serum proteins and their subunits, compared to literature picture (18) of two dimensional (2D) iso-electric pH followed by SDS reduced gel electrophoresis analysis of plasma showing its complexity.

Electrophoresis 1 dimensional polyacrylamide gel electrophoresis (1D PAGE) was used to analyze and visualize both the partitioning of proteins in ATPS as well as the precipitation of plasma proteins with PAA. 10 µl of the sample to be analyzed was added to 10 µl of SDS-PAGE loading buffer containing 50% NuPAGE LDS Sample buffer (4×) (Invitrogen, Carlsbad, Calif., USA) and 20% (w/w) β-mercaptoethanol and the mixture was reduced by heating at 70° C. for 10 min. The samples were cooled and 10 µl loaded onto a NuPage® 4-12% Bis Tris gel (Invitrogen, Carlsbad, Calif., USA) and analyzed alongside 5 µl of Precision Plus® protein uni-stained molecular weight markers (Biorad, Hemel Hempstead, UK). Electrophoresis was performed in NuPage MOPS SDS Running Buffer (20×) (Invitrogen, Carlsbad, Calif., USA) at 150V for one hour. Protein bands were stained using GelCode Blue® (Coomassie-type) stain reagent (Thermo Fisher Scientific, Waltham, Mass., USA) with shaking over night before destaining in MilliQ water for 24 hours. The 1D gel analysis provides insight into the relative distribution of major plasma proteins in blood and in other samples (e.g. separated fractions) (FIG. 4).

Figure 5:
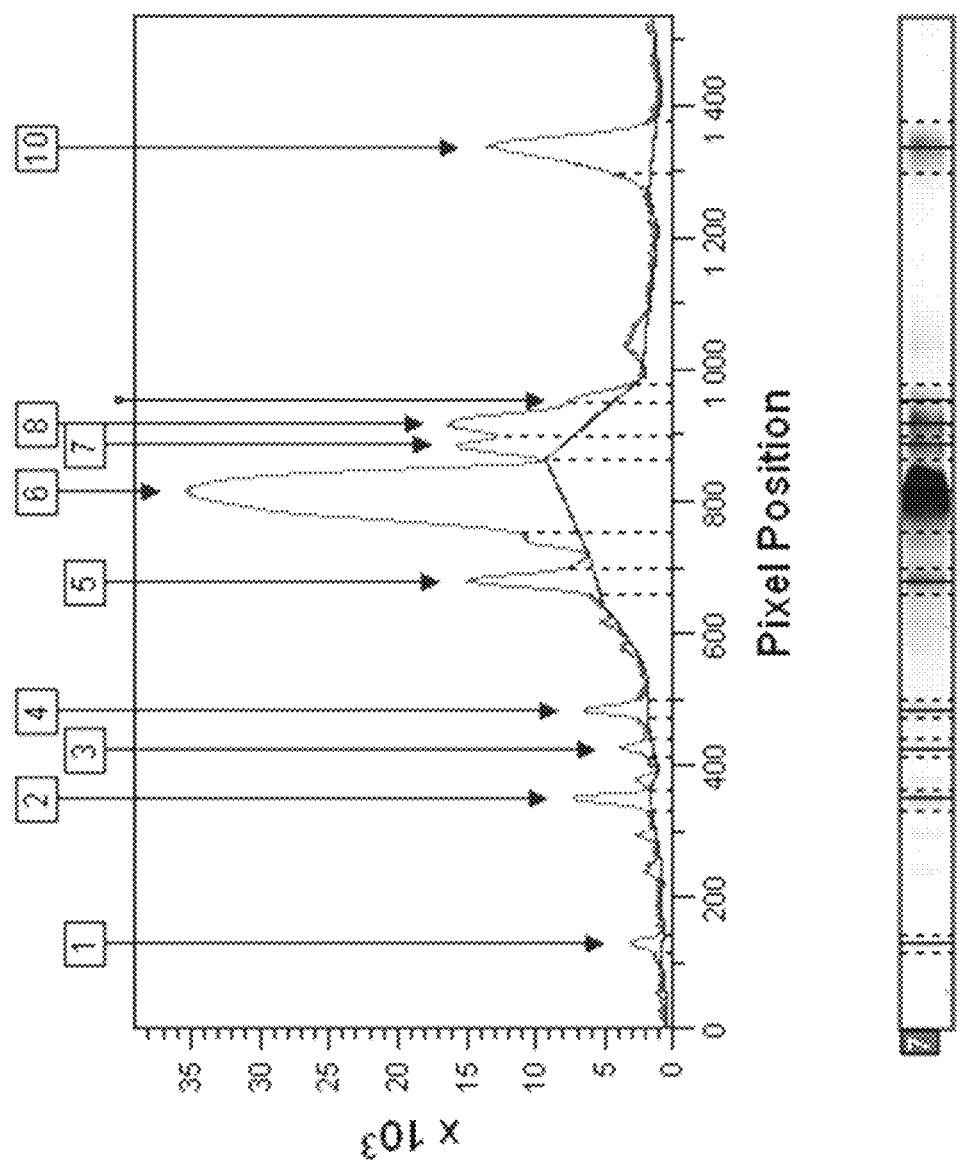
FIG. 5. 1D reduced SDS gel electrophoresis analysis of human plasma (to the left with increasing MW from bottom to top) is shown versus ImageQuantTL™ analysis of the relative intensity of each of ten major bands (peaks) and their relative pixel position. The number 7 at the top of the SDS gel refers to the lane. The gel contains many other reproducible peaks related to proteins of lesser abundance.

ImageQuantTL™ (GE Healthcare, Uppsala, Sweden) software was used to analyze the molecular weight and the relative amount of each band in each lane of the gel, i.e. the percentage of each protein in the sample out of the total amount of protein in the sample (FIG. 5). The molecular weight of the protein was calculated with the aid of a standard curve based on the molecular weight marker. The relative amount of each protein is estimated based on the intensity of the protein band in comparison with the other bands in the lane.

Accuracy of Image Analysis and Quantification

By the above method the ten major protein peaks shown in FIG. 5 had relative MW (kDa) abundances (% of total) of 1=374 kDa, 1.1%; 2=190 kDa, 2.6%; 3=139, 1.1%; 4=119 kDa, 2.2%; 5=77 kDa, 6.3%; 6=60 kDa, 55.4%; 7=55 kDa, 4.7%; 8=53 kDa, 10.5%; 9=52 kDa, 1.6%, and 10=25 kDa, 14.5%. Thus it is expected that band 5 probably represents transferrin, band 6 albumin, bands 8 and 10 Ig light chain subunits, bands 7 and 9 fibrinogen subunits. Albumin is generally taken to represent 60% of the total protein, transferrin 4%, and IgG 20% (heavy and light chains) so that within reason for human sample variation and different analysis methods (optical dye quantification versus protein analysis) the ImageQuantTL image analysis allows for fairly accurate analysis of protein.

However this method is more accurate for proteins of high concentrations such as albumin than proteins of low concentrations such as fibrinogen. It also requires accurate identification of protein bands. It is expected that the different subunits of the proteins (such as Ig) would be present at the same abundance which is not the case. In this plasma sample only two bands can be seen for fibrinogen, the third band is probably hidden by the albumin band since their molecular weight is quite similar. Some Ig protein may show up in bands thought to relate to fibrinogen subunits. Another concern is that assigning which protein relates to which band in the electrophoresis gel is also an estimation based on the calculated molecular weight standard curve and the relative position of the protein bands. This analysis method gives a good estimate of the amount of each protein in the sample but it is just an estimate. It also has to be kept in mind that plasma is a complex mixture of proteins and that the Ig levels can vary significantly from person to person, and even for one individual over a few hours based on the individual's health.

The information obtained from the ImageQuantTL analysis was used together with the information from the Biuret assay to estimate the total protein concentrations in the samples as well as the sample concentration of individual plasma proteins.

Biuret Assay

For quantification of the protein concentration in the supernatants and precipitates respectively the Biuret assay was used. The Biuret assay is a chemical assay used to detect the presence of peptide bonds with the aid of copper (II) ions. The copper (II) ions form a violet-colored complex in the presence of peptide bonds and the absorption measured at 540 nm is directly proportional to the protein concentration according to Lambert-Beer law.

Depending on the expected concentrations in the samples a high or a low standard curve was prepared. The high standard curve ranged from 80 mg/ml to 5 mg/ml and the low standard curve from 5 mg/ml to 0.5 mg/ml. The standards were prepared using an 80 mg/ml protein standard containing human serum albumin and gamma-globulin (Sigma Aldrich, St. Louis, USA). When the high standard curve was used, 10 µl of standard was added in duplicates to a 96-well microtiter plate (Grenier Bio-One, US) as well as 10 µl and 5 µl aliquots of each sample in duplicates. When the low standard curve was used 100 µl of standard was added in duplicates to a 96-well microtiter plate as well as 100 µl aliquots of each sample, also in duplicates. MilliQ water was used as blank as well as PAA diluted in MilliQ to examine whether the PAA interfered with the assay or not. 200 µl of Biuret solution was thereafter added to each well and the plate was incubated for 30 min on a shaking board and the absorbance was subsequently monitored in a spectrophotometer (SPECTRA max PLUS$^{384}$, Molecular Devices, Sunnyvale, Calif., USA) at 540 nm. The concentration of protein in the supernatants and precipitates was determined with aid of the standard curve. To be able to compare the concentration in the precipitate with the concentration in the supernatant the concentration in the precipitate was back-calculated to 5 ml as follows Precipitate concentration=([precipitate]*resuspension volume)/5 ml) [4]

To quantify the concentration of individual proteins in the plasma samples (precipitates and supernatants) the percentage of each protein in each sample obtained when analysing the electrophoresis gels with ImageQuantTL (see above) was multiplied by the total protein concentration in each sample obtained from the Biuret assay, see below;

Concentration of Individual Proteins in the Precipitates and Supernatants;

Concentration of a single type of protein in a plasma or plasma fraction or band sample was calculated as follows:

Concentration (mg/ml)=% of the protein in the sample (ImageQuantTL)×the total protein concentration in the sample (Biuret assay) (mg/ml) [5]

To validate the accuracy of the concentrations obtained with the Biuret assay the total protein concentration in the starting samples—precipitate (ppt)+supernatant (sup)—was calculated as well as the total concentration of the individual proteins in the starting samples (ppt+sup) and compared with estimated values. Plasma samples normally have a total protein concentration of approximately 70 g/l and when diluted 3.3 times in the samples (1.5 ml plasma in 5 ml systems) the total protein concentration in the starting samples (ppt+sup) is expected to be around 23 g/l. Major plasma protein concentrations in the starting experimental sample are therefore expected to approach albumin ~14 g/l, IgG ~4.7 g/l and fibrinogen ~1.2 g/l which is in keeping with their normal values (Table 1) diluted 3.3×. To quantify the percentage of the individual proteins that precipitate at different sample conditions the concentration of the individual protein in the precipitate (calculated as described above) was divided with the total concentration of that protein in the starting sample (ppt+sup).

HiTrap™ Q Sepharose™ Fast Flow Chromatography

The precipitation of purified plasma proteins was investigated at varying concentrations of PAA. Appropriate volumes of human serum albumin (HSA), gamma globulin (Gammanorm) and monoclonal antibody were dissolved in MilliQ water to reach a final concentration of 5 mg/ml. The HSA sample was subsequently filtered with 0.45 µm sterile filter (Sarstedt, Nümbrecht, Germany). Precipitation of the proteins was performed as noted above and the result was examined spectro-photometrically (see above). At a PAA concentration above 7% (w/w) the polymer appeared to significantly interfere with the $A_{280}$-analysis. In order to reduce the PAA concentration, the supernatants were filtered with 0.45 µm sterile filter (Sarstedt, Nümbrecht, Germany) and 1 ml was loaded on to a HiTrap™ Q Sepharose™ Fast Flow column (GE Healthcare, Uppsala, Sweden) pre-packed with Q Sepharose (quaternary amine based strong anion exchanger) placed in an ÄKTA™ explorer (GE Healthcare, Uppsala, Sweden) controlled with Unicorn™ software (GE Healthcare, Uppsala, Sweden). The eluant was monitored at 280 nm, 260 nm and 220 nm. PAA, diluted in water to reach the sample concentrations of PAA, and the standard protein solutions were loaded on to the column. The protein concentration in the supernatants was calculated as $A_{280}$ (supernatant)–$A_{280}$ (blank). The protein concentration in the precipitate could then be calculated as $A_{280}$ (standard)–$A_{280}$ (supernatant).

Biacore™ Based Surface Plasmon Resonance Analysis

To evaluate the reliability of the protein concentration estimated with the aid of the SDS-PAGE analysis and the Biuret assay, Biacore based analysis was used to analyze the concentrations of IgG in some of the precipitates and supernatants. The instrument used in this study was a Biacore™ T100 (GE Healthcare, Uppsala, Sweden) and the chip a Series S Sensor Chip CM5 (carboxymethyldextran coated) from GE Healthcare (Uppsala, Sweden) Immobilization of antibodies, monoclonal anti-human IgG (Fc) from mouse (part of Human Antibody Capture Kit™, GE Healthcare, Uppsala, Sweden), to the chip was performed with Amine Coupling Kit™ (GE Healthcare, Uppsala, Sweden) using a standard protocol from the manufacturer. All supernatants were diluted 100 times (10 µl+990 µl) followed by two two-fold dilutions and the precipitates were diluted 200 times (5 µl+995 µl) followed by three two-fold dilution with HBS-EP+buffer (buffered saline) in order to fit within the standard curve. The standard curve ranged from 50 µg/ml to 0.512 µg/ml with a dilution factor of 2.5 (240 µl+360 µl buffer). The standard was prepared with human IgG from Sigma-Aldrich (St. Louis, USA). The samples were injected for 20 seconds at a flow rate of 20 µl/min. Regeneration was performed for 30 seconds with 3M $MgCl_2$ (part of Human Antibody Capture Kit, GE Healthcare, Uppsala, Sweden) at a flow rate of 30 µl/min. Control samples, prepared with human IgG from Sigma-Aldrich (St. Louis, USA), of 20

µg/ml and 1.28 µg/ml were used. Startup cycles were performed at 8 µg/ml and prepared with the same antibody as the standard curve and the control samples.

Conductivity Measurements

Figure 6:
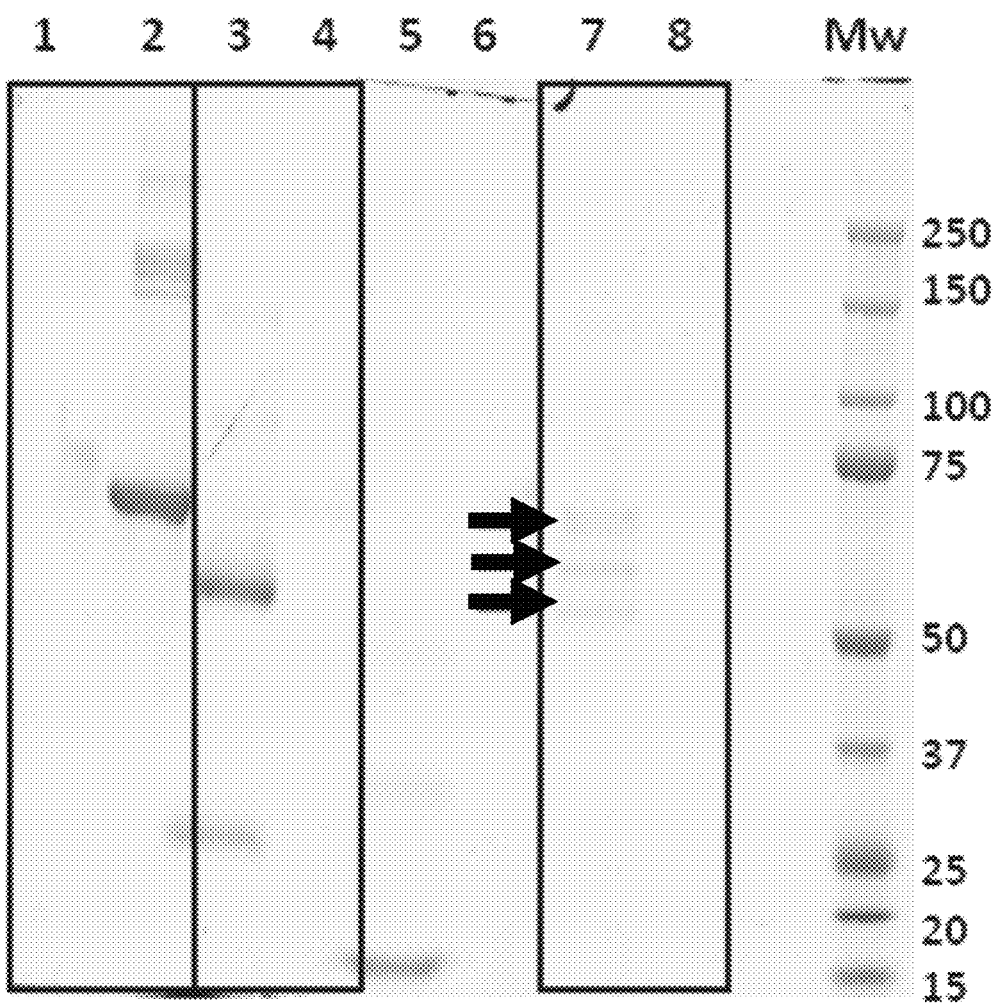
FIG. 6. 1D reduced SDS gel electrophoresis analysis of human plasma proteins partitioned in representative EOPO phase system (i.e., 8% EOPO, 150 mM NaCl, 100 mM NaCitrate, pH7, 40° C.) believed to be useful for blood clarification and protein isolation. Lane; 1—HSA polymer phase, 2—HSA water phase, 3—IgG water phase, 4—IgG polymer phase, 7—Fibrinogen—water phase, 8—Fibrinogen polymer phase. Three fibrinogen subunits in lane 7 shown with arrows.

The conductivity of the systems was measured. The systems were prepared by mixing appropriate volumes of plasma, citrate buffer, sodium chloride and PAA to reach desired concentration, and the volume was altered to 1 ml with MilliQ water. The conductivity was monitored with a Pharmacia Conductivity Monitor (Pharmacia Biotech, now GE Healthcare, Uppsala, Sweden).

phases of all three systems were analyzed by $A_{280\,nm}$ spectrophotometry and SDS-PAGE to study the partitioning of the three proteins between the phases. The results for all three systems are presented in Table 3 and representative electrophoresis analysis (for system 1 results) are shown in FIG. 6.

TABLE 3

$A_{280}$-analysis of Plasma Protein Partition in EOPO Single Polymer Phase Systems ATPS System 1—8% EOPO, 150 mM NaCl, 100 mM NaCitrate (pH7), 40° C.

| Protein | $A_{280}$ Up. phase (water-rich) | $A_{280}$ Low. phase (polymer) | Phase Volumes (w/p) | $AU_{280}$ * | Ref. | G | c/o (%) | Estimated Recovery (%) |
|---|---|---|---|---|---|---|---|---|
| HSA | 0.72 | 0.02 | 4.2/0.8 | 3.04 | 2.45 | 189 | 99.47 | 124 |
| IgG | 1.31 | 0.00 | 4.2/0.8 | 5.50 | 5.6 | >1000 | 100 | 98.2 |
| Fib. | 0.61 | 0.00 | 4.2/0.8 | 2.56 | 0.75 | >1000 | 100 | >100** |

ATPS System 2—ATPS 2: 8% EOPO 150 mM NaCl, 250 mM NaCitrate (pH 7), RT

| Protein | $A_{280}$ Up. phase (polymer) | $A_{280}$ Low. phase (water-rich) | Phase Volumes (w/p) | $AU_{280}$ * | Ref. | G | c/o (%) | Estimated Recovery (%) |
|---|---|---|---|---|---|---|---|---|
| HSA | 0 | 0.65 | 1.3/3.7 | 2.40 | 2.75 | >1000 | 100 | 87 |
| IgG | 0 | 1.53 | 1.3/3.7 | 5.66 | 5.55 | >1000 | 100 | 102 |
| Fib. | 0 | 0.26 | 1.3/3.7 | 0.96 | 2.55 | >1000 | 100 | 37.6 |

ATPS System 3—8% EOPO, 150 mM NaCl, 100 mM NaCitrate (pH7), 40° C.

| Protein | $A_{280}$ Up. phase (water-rich) | $A_{280}$ Low. phase (polymer) | Phase Volumes (w/p) | $AU_{280}$ * | Ref. | G | c/o (%) | Estimated Recovery (%) |
|---|---|---|---|---|---|---|---|---|
| HSA | 0.6 | 0.23 | 4.2/0.8 | 2.7 | 2.6 | 13.7 | 93.2 | 104 |
| IgG | 1.42 | 0.37 | 4.2/0.8 | 6.26 | 6.1 | 20 | 95.2 | 102.6 |
| Fib. | 0.88 | 0.00 | 4.2/0.8 | 3.7 | 1.15 | >1000 | 100 | >100** |

*$A_{280,w}$ × phase volume + $A_{280,p}$ × phase volume
** Fibrinogen recovery was difficult to measure due to the low levels of protein studied.

Example 1. Partitioning of Plasma Proteins in ATPS

Representative, purified, samples of major plasma proteins were partitioned in aqueous two phase systems (ATPS). The partitioning of HSA, human Ig (Gammanorm) and fibrinogen was examined in three different systems;

1. 8% EOPO 150 mM NaCl, 100 mM NaCitrate (pH 7), 40° C.
2. 8% EOPO, 150 mM NaCl, 250 mM NaCitrate (pH 7), RT.
3. 8% EOPO 150 mM NaCl, 100 mM NaPhosphate (pH 7), 40° C.

In all three systems a two-phase system was rapidly established. In system 1 and 3 the polymer-rich phase (p-phase) was denser than complementary phase and was found in the bottom of the container. In system 2 phase separation occurred at room temperature and the salt containing water-rich phase was denser, making it relatively easy to isolate by draining off. The polymer- and water-rich phases of all three systems were analyzed.

All three of the major plasma proteins studied partitioned significantly to the water-rich phase. Fibrinogen results were based on relatively low concentrations of protein and appear somewhat variable. Some fibrinogen aggregation in system 2 may have affected its estimated recovery. However lack of fibrinogen absorbance in the polymer-rich phases, or fibrinogen protein bands in the electrophoresis gels related to the polymer-rich phase support the conclusion that fibrinogen partitioned significantly to the water-rich phase in all three systems.

Example 2. Precipitation of Plasma Proteins with Polyacrylic Acid

Figure 7:
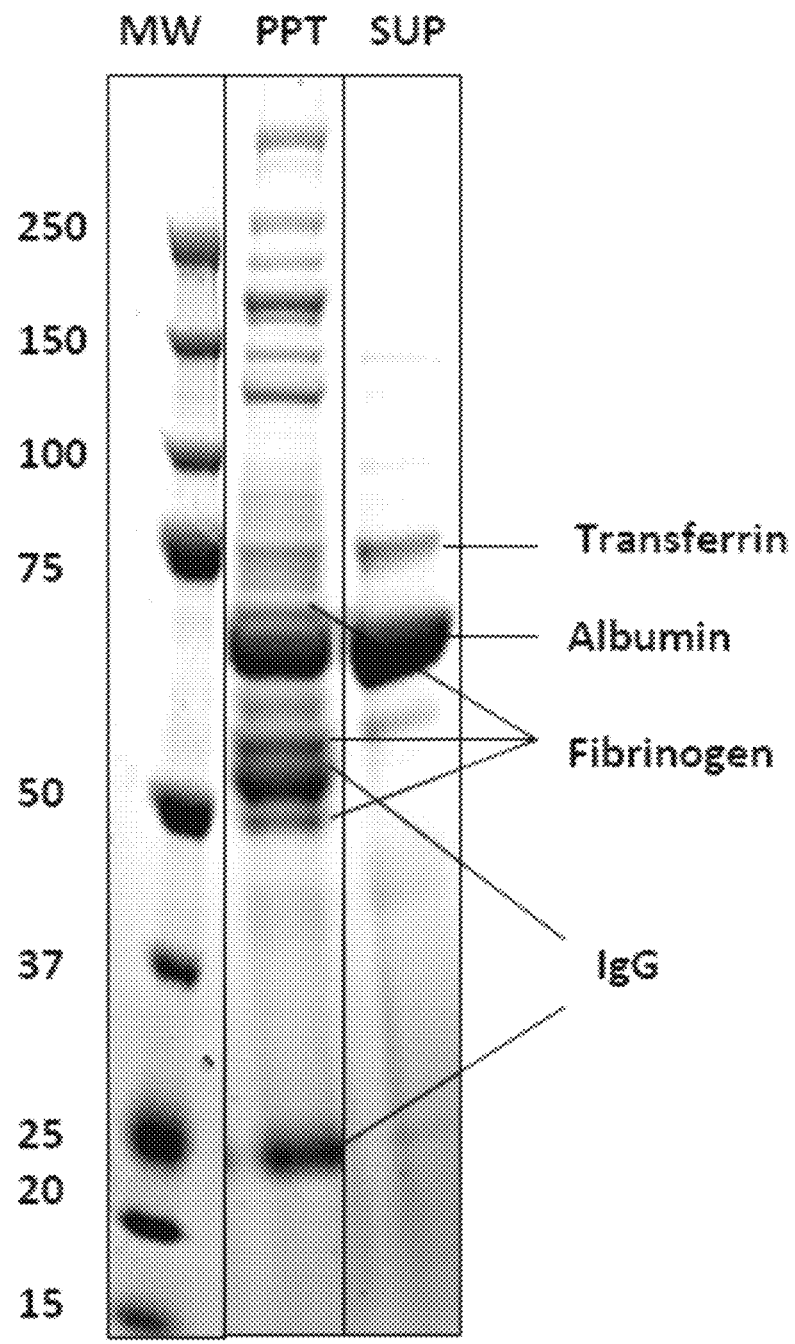
FIG. 7. 1D reduced SDS gel electrophoresis analysis of human plasma proteins precipitated with aid of 10% polyacrylic acid. Most serum proteins precipitate while much of the albumin (HSA) and transferrin appear to remain in the supernatant. System (5 ml): 1.5 ml plasma, 10% (w/w) PAA 15 000, 250 mM NaCitrate pH 7, 150 mM NaCl.

A system of 10% (w/w) PAA (15000), 250 mM NaCitrate (pH 7) and 150 mM NaCl (prepared as noted above) was chosen for initial fractionation of plasma sample with analysis performed according to the methods also noted above. Electrophoresis results for supernatant and resuspended precipitate are shown in FIG. 7. Most serum proteins including fibrinogen and antibody protein precipitated while much of the albumin (HSA) and transferrin appeared to remain in the supernatant.

Example 3. Precipitation of Purified Plasma Proteins with Polyacrylic Acid

Inclusion of NaPhosphate, NaCitrate or similar chaotropic salt together with PAA in the present work appears to provide an avenue for much more robust process (example 2 above) where one might only have to alter PAA concentration to effect selectivity. This was first tested using purified plasma proteins HSA, IgG and Mab and precipitation systems containing 5%, 7% and 9% (w/w) PAA together with 50 mM NaCitrate and 50 mM NaCl, pH 7. The analysis of supernatant was performed using HiTrap™ Q Sepharose™ Fast Flow as noted above with results expressed as percentage of the total protein relative to the control. The reference was 5 mg/ml protein solution without added PAA 15000. Results are noted in Table 4.

Differences in the polarity, conductivity or other properties of experimental solutions containing PAA versus control solutions may have resulted in some values over 100%. It can be see that the tendency for PAA to precipitate plasma proteins out of solution follows the same general order as in ethanol (i.e. Cohn Fractionation) based precipitation (i.e. fibrinogen then antibody then albumin) The results suggest some protein selectivity based on PAA concentration. Other factors are explored in the examples below. Note that the analysis method does not necessarily measure all precipitation (flocculation) particles which might be suitable bioprocessing using filtration or other capture methods. Some antibody precipitation noted visually as solution clouding at 5% PAA did not appear in the data—perhaps due to small microcomplexes not precipitate down under the centrifugation conditions of these initial studies. The results, which appear similar to results with real plasma (see below) suggest the different types of proteins are behaving somewhat independently of each other even when precipitated from complex solution such as plasma. They also suggest that while PAA concentration variation (i.e. of 1% w/w) may allow for some control over selectivity the general method is robust and will not be adversely affected by slight variation (i.e. 0.2% w/w) in polymer concentration, PAA polymer sample MW or other properties.

TABLE 4

Relative Protein in Supernatants Exposed to Precipitation with Varying PAA Concentration.

| Protein | Reference Value (100% of protein) | 5% (w/w) PAA (% of protein) | 7% (w/w) PAA (% of protein) | 9% (w/w) PAA (% of protein) |
| --- | --- | --- | --- | --- |
| HSA (mAU * ml) | 511 | 105 | 116 | 114 |
| Polyclonal IgG (mAU * ml) | 1514 | 108 | 80 | 19 |
| mAb (mAU * ml) | 2105 | 85 | 53 | 3 |

Example 4. Effect of PAA MW on Precipitation of Plasma Proteins

Polyacrylic acid polymer solutions tend to increase significantly in viscosity as polymer molecular weight increases. In addition higher MW PAA polymers tend to exhibit a wider range of MW and thus be less reproducible in their solution performance. As polymer size increases it was expected that any residual polymer might be more difficult to isolate from target protein (e.g. using filtration or size exclusion chromatography) and may more readily foul filtration or chromatography beds used in further purification of target protein. It was therefore decided to look at the effect of varying PAA MW 8000 versus 15000 using 10% (w/w) PAA, 250 mM NaCitrate and 150 mM NaCl. In both experiments electrophoretic analysis results (not shown) were almost identical to those shown for 10% PAA 15000 in FIG. 7 emphasizing the robustness of the method.

Example 5. Effect of Polymer Acid Type, MW, and Substitution

The following three different polymer based precipitation systems (experiments) were studied; Polyvinylsulfonic acid (PVS) 5 ml final volume solution consisting of 1.5 ml plasma, 200 mM NaCitrate (pH7), 11% (w/w) PVS (3000 MW), MilliQ water to 5 ml; Carboxymethyldextran (CMD) of 1.25 ml final volume solution consisting of 0.4 ml plasma, 200 mM NaCitrate (pH 7), 20% (w/w) CMD (40000 MW, DS 1.39), MilliQ water to 1.25 ml; Polyacrylic Acid (PAA) 5 ml final volume consisting of 1.5 ml plasma, 200 mM NaCitrate (pH 7), 10% (w/w) PAA (15000, MilliQ water to 5 ml final. Polymer concentrations were varied slightly balance of ionized groups based on pKa or degree of substitution (DS) in the case of CMD. Note that the polymers represent different molecular weights (3 000 to 40 000) and three different acid groups (FIG. 8), different polymer concentrations (10 to 20%) and different degrees of substitution—based on monomer group to acid moiety ratios of 1 to 1.39 (see above). As indicated by the electrophoresis results in FIG. 8 all three polymers functioned well, and provided almost identical precipitation selectivity, under conditions which included 200 mM of NaCitrate pH 7. All resulted in protein-polymer complexes readily separable from supernatant via low level (4 000 rpm) desktop centrifugation. The method of using the polyacid together with a lyotropic salt such as NaCitrate thus appears very robust. Further robustness was demonstrated in the next experiment which was related to effects of polyacid concentration.

Example 6. Selectivity Effect of Polyacrylic Acid Concentration

Figure 9:
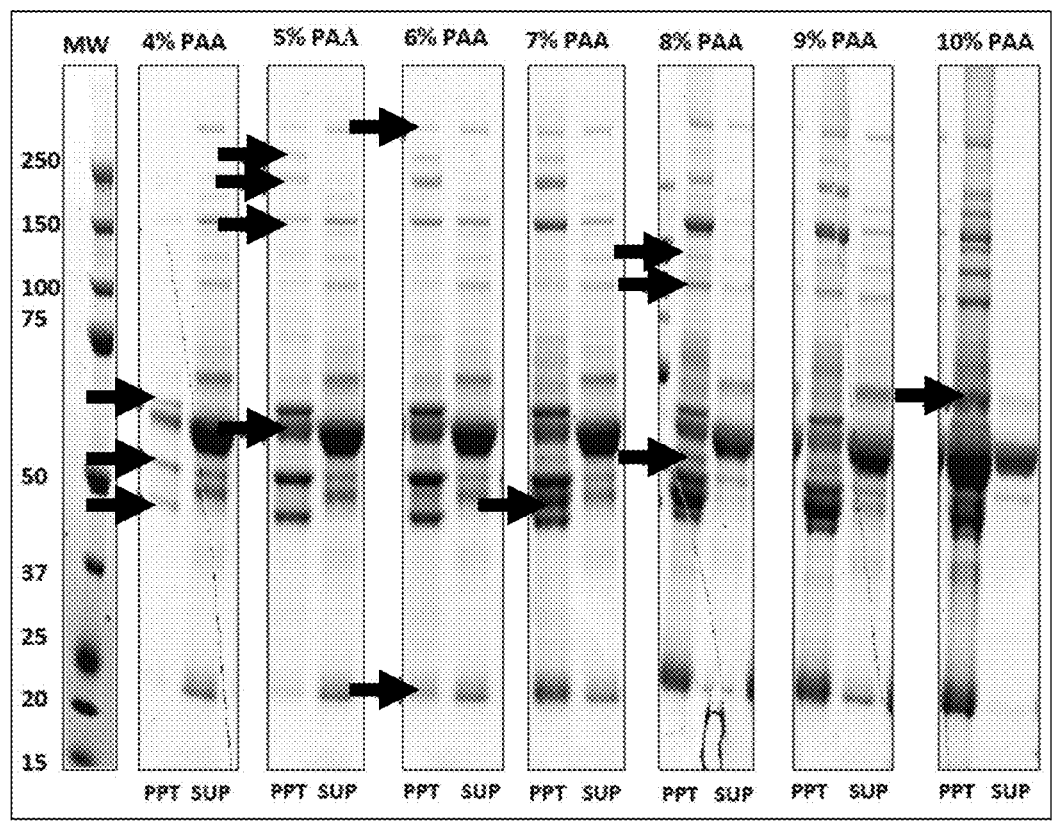
FIG. 9. 1D reduced SDS gel electrophoresis analyses showing the effects of adding polyacrylic acid (PAA 15 000) at different concentrations (4 to 10% w/w) to 5 ml plasma precipitation solutions consisting of 1.5 ml plasma, 50 mM NaCitrate, pH 7, 50 mM NaCl. Precipitate (PPT) and supernatant (SUP) fractions were analysed. Appearance of new prominent protein bands are indicated by arrows.

FIG. 9 shows 1D reduced SDS PAGE analyses related to the effects of adding polyacrylic acid (PAA 15000) at different concentrations (4 to 10% w/w) to 5 ml plasma precipitation solutions consisting of 1.5 ml plasma, 50 mM NaCitrate, pH 7, 50 mM NaCl. Precipitate (PPT) and supernatant (SUP) fractions were analysed as described above under Methods. First significant appearance of some protein bands in the gels are shown by arrows. These results are in keeping with those for pure plasma proteins shown in Example 3. It can be seen that as polyacid concentration is increased different proteins tend to precipitate. It would appear that some selectivity in isolation of plasma proteins present in significant concentrations (and in some cases proteins present in minor concentration) can achieved simply by varying polyacid concentration—without need to add solvent or alter pH or salt concentration. Robustness of the method is such that different proteins can be selectively precipitated on going from 4 to 10% however slight operational variation in polyacid concentrations (e.g. +/−0.2% w/w) should not appreciably affect the results. Note that this study was effected using salt concentration of 50 mM NaCitrate and 50 mM NaCl compared to 200 mM NaCitrate in Example 5. This also provides some insight to the robustness of the general approach. More ionic strength effect data is shown in later examples.

Given that plasma has a total protein concentration of around 70 g/l and is diluted approximately three times in the experiments (i.e. 1.5 ml plasma to 5 ml total), the total protein concentration in the systems is expected to be approximately 23 g/l. HSA normally contributes to 60% of the total protein mass, Ig's 20%, and fibrinogen 5%. Thus one might expect population averaged mg/ml values of approximately 14, 5 and 1.2 mg/ml respectively for HSA, Ig and fibrinogen which compares favorably to the Biuret assay measured values of 13, 5 and 1.3 (data not shown) in the starting samples.

The precipitate and supernatant fractions were analysed for antibody by Biacore SPR assay and the major protein gel electrophoresis bands from Coomassie type staining with GelCode Blue were further analysed by ImageQuantTL analysis. In addition major protein band MW estimates were used for protein (subunit) identification. These results are discussed below.

The PAGE results (FIG. 9) suggest that at a PAA concentration below 7% (w/w) there is mainly fibrinogen in the precipitate together with what to appear to be varying amounts of one or more proteins of approximately 60 kDa. This could represent a small percentage of HSA or it might represent other protein chains such as those related to IgD, IgA or IgM. At 6% (w/w) PAA, plasma IgG starts to precipitate as indicated by its light chains around 20 kD and when the PAA concentration reaches 10% (w/w) almost all of the plasma proteins precipitate; including some of the HSA. A significant part of the globular protein HSA sample and a slightly larger protein (assumed to be the globular protein transferrin) remain in solution. The Biacore and ImageQuant TL analyses of total protein and protein fractions support the above general interpretation.

Figure 10:
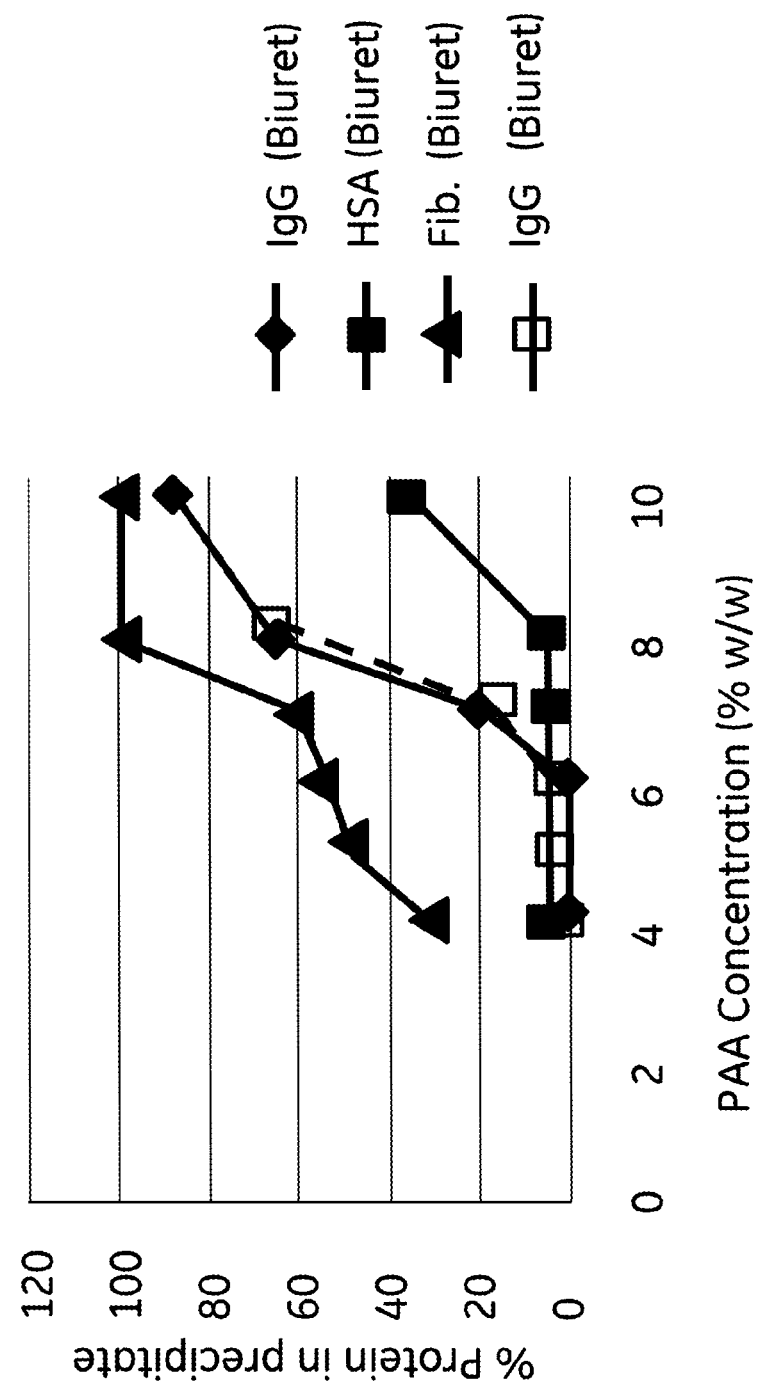
FIG. 10. Percentage of the total amount of IgG, HSA and fibrinogen found in the precipitate as a function of the PAA concentration. Data based on ImageQuantTL analysis of FIG. 9 electrophoresis. Also shown are Biacore SPR analytical results for antibody.

FIG. 10 shows the estimated percentage of individual fibrinogen, IgG and albumin (HSA) protein in the precipitates as a function of the PAA concentration. ImageQuantTL analytical results suggest only 30% of the fibrinogen is precipitating at 4% PAA whereas to the eye the electrophoresis gels would suggest more fibrinogen is precipitated. This may be due to nonlinearity of the optical approach and reduced sensitivity of the image analysis at lower protein concentrations. Regardless the data suggest it should be possible to identify PAA concentration ranges where major protein fractions are selectively precipitated. Note that in the above examples only PAA concentration was varied so that at each concentration many proteins competed with each other to varying degrees for inclusion in the precipitate complex. As the proteins differ considerably in size, diffusivity, net charge and other factors (inherent hydrophobicity and solubility) this may have contributed to reducing the slope of the linear regions of the data in FIG. 10. As a result better selectivity was expected to occur if polymer concentration and precipitation were varied in step-wise fashion per the next example.

Figure 11:
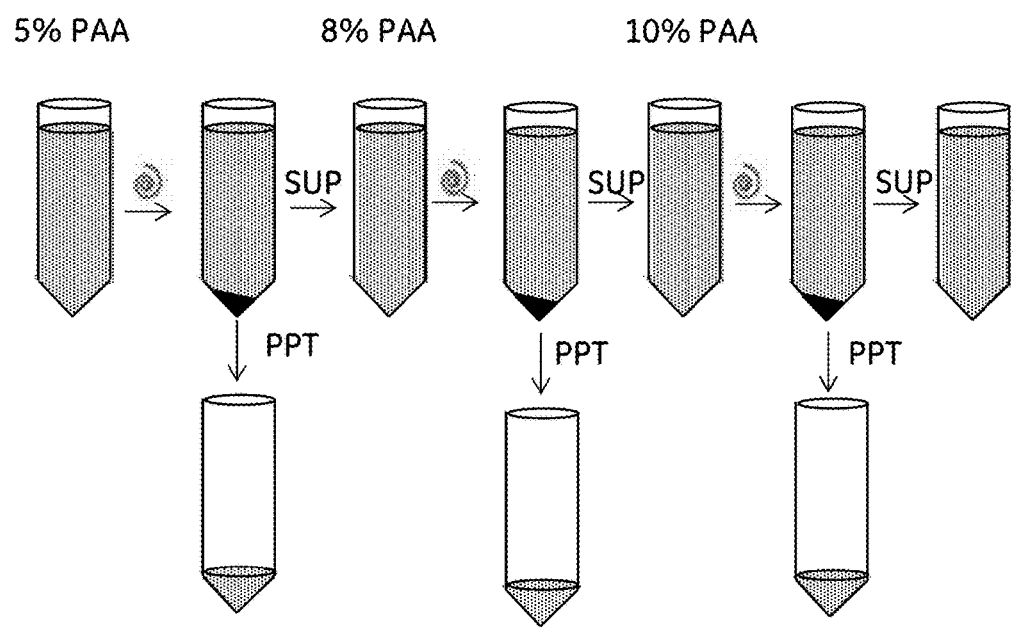
FIG. 11. Three-step, four-fraction, process for fractionation of plasma in solutions containing varying % w/w concentration of polyacrylic acid (PAA) and at least 50 mM NaCitrate, pH 7. 5% PAA is added then following isolation of the precipitate by sedimentation, filtration or centrifugation (shown) supernatant concentration is raised to 8% PAA and then, following isolation of the precipitate, supernatant concentration is raised to 10% PAA. The precipitate is then resuspended leaving three precipitate fractions and a final supernatant fraction.
Figure 12:
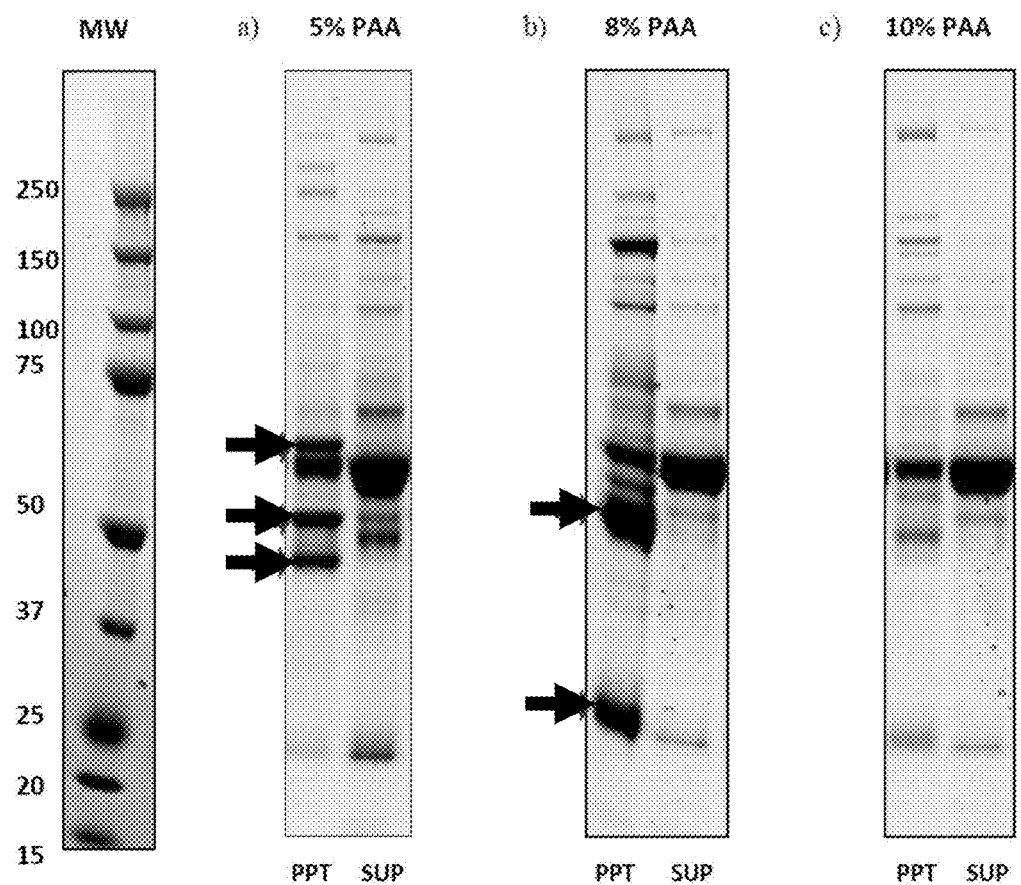
FIG. 12. 1D reduced SDS gel electrophoresis showing sequential fractionation of plasma proteins with increased concentration of PAA per FIG. 11. System (5 ml): 1.5 ml plasma, 4-10% (w/w) PAA (15 000), 50 mM NaCitrate (pH 7), 50 mM NaCl.

Example 7. Three Step Plasma Fractionation Approach Based on Three PAA Concentrations FIG. 11 shows a possible three step fractionation of plasma based on the above results. Note that the process results in four fractions—three precipitate fractions, which can be resuspended, and one final supernatant fraction. FIG. 12 shows 1D reduced PAGE showing sequential fractionation of plasma proteins with increased concentration of PAA per FIG. 11. System (5 ml): 1.5 ml plasma, 4-10% (w/w) PAA (15000), 50 mM NaCitrate (pH 7), 50 mM NaCl. In these experiments the PAA concentration was adjusted assuming that a relatively small inconsequential amount of PAA was removed in the previous precipitation step. Results are in keeping with those in Example 6 however the protein fractions appear cleaner due to removal of complex forming protein in the previous precipitation step.

TABLE 5

Estimated (mg/ml) concentration of fibrinogen, IgG and albumin (HSA) in the 5 ml supernatants and 5 ml resuspended precipitates from fractionation per FIG. 12.

| Protein | 5% PPT | 5% SUP | 8% PPT | 8% SUP | 10% PPT | 10% SUP |
|---|---|---|---|---|---|---|
| HSA (mg/ml) | 0.42 | 11.96 | 0.36 | 10.76 | 0.45 | 9.39 |
| IgG (mg/ml) | 0.04 | 5.02 | 2.08 | 0.51 | 0.16 | 0.33 |
| Fibrinogen (mg/ml) | 0.9 | 0.9 | 0.09 | 0 | 0 | 0 |

TABLE 6

% of total individual protein recovered, estimated from Table 5.

| Protein | 5% PAA PPT | 8% PAA PPT | 10% PAA PPT | 10% PAA SUP | Total |
|---|---|---|---|---|---|
| HSA (%) | 4.0 | 3.4 | 4.2 | 88.4 | 100 |
| IgG (%) | 1.5 | 79.7 | 6.2 | 12.6 | 100 |
| Fibrinogen (%) | 91.0 | 9.0 | 0 | 0 | 100 |

Table 5 shows the estimated (mg/ml) concentration of fibrinogen, IgG and albumin (HSA) in the 5 ml supernatants and (5 ml resuspended) precipitates from fractionation per FIG. 12. Total protein determined via Biuret assay and relative amounts per PAGE band (FIG. 13) determined via ImageQuantTL analysis of Coomassie stained gels. As noted above, based on normal plasma values one expects the sums of the 5%, 8% and 10% precipitate and 10% supernatant values for HSA Ig, and fibrinogen to be approximately 14, 5, and 1.2 which compares reasonably well to the measured total values of 13, 5 and 1.3, suggesting the recovered values of 10.6 (82%), 2.6 (52%) and 1.0 (77%) for HAS, Ig and fibrinogen. Tendency of ImageQuantTL estimates to be lower than expected could be due to effects of PAA on protein-dye interactions, the large number of low abundance protein bands in each gel, and mistaken assignment of proteins bands. In particular IgG estimates may be lower than expected due to the complexity of the antibody subtypes present, and their relative sensitivity to reduction; as well as the tendency of IgG subunit gel bands and to overlap in MW with bands of other proteins. The above calculated values are expected to have rather large standard errors (perhaps +/−0.1 of the noted values) but even allowing for such error verify that the approach in FIG. 11 can result in three fractions (5% PPT, 8% PPT and 10% SUP) each containing a majority of the fibrinogen, IgG and HSA proteins. The electrophoresis results shown in FIG. 12 also suggest the four fractions are enriched in other (as yet unidentified) proteins of possible biomedical interest of which a significant amount appear in the 10% PAA precipitate. Ability of the sequential approach to improve on the purity of each fraction in regard to fibrinogen, IgG and HSA may be related to relative decrease in total protein or specific protein type competing for complex formation in each step.

It is expected that the significant amount of HSA in the 10% PAA supernatant might be precipitated in further step involving a higher concentration of PAA. In the above example when PAA concentration was raised to 15% over 35% of the albumin could be precipitated (data not shown). Increasing salt concentration further increased albumin precipitation (see below). Capturing albumin in precipitate form may be useful for volume reduction and interim storage of the HSA prior to further processing. It might also facilitate resuspension of the precipitates in solution with lower net concentration of PAA. However it is expected that the 10% soluble fraction may also be readily subjected to further purification (including isolation of the PAA from the protein) via filtration and chromatography.

Example 8. Effect of Conductivity

Figure 13:
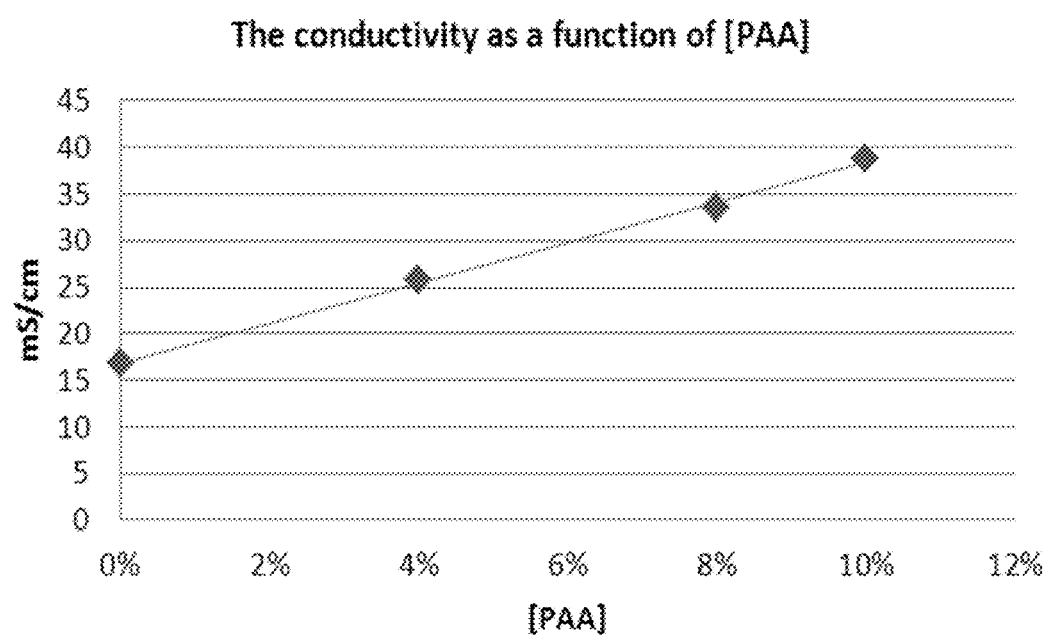
FIG. 13. Conductivity versus PAA 15 000 concentration (% w/w) in solution containing 50 mM NaCl and 50 mM NaCitrate, pH 7.
Figure 14:
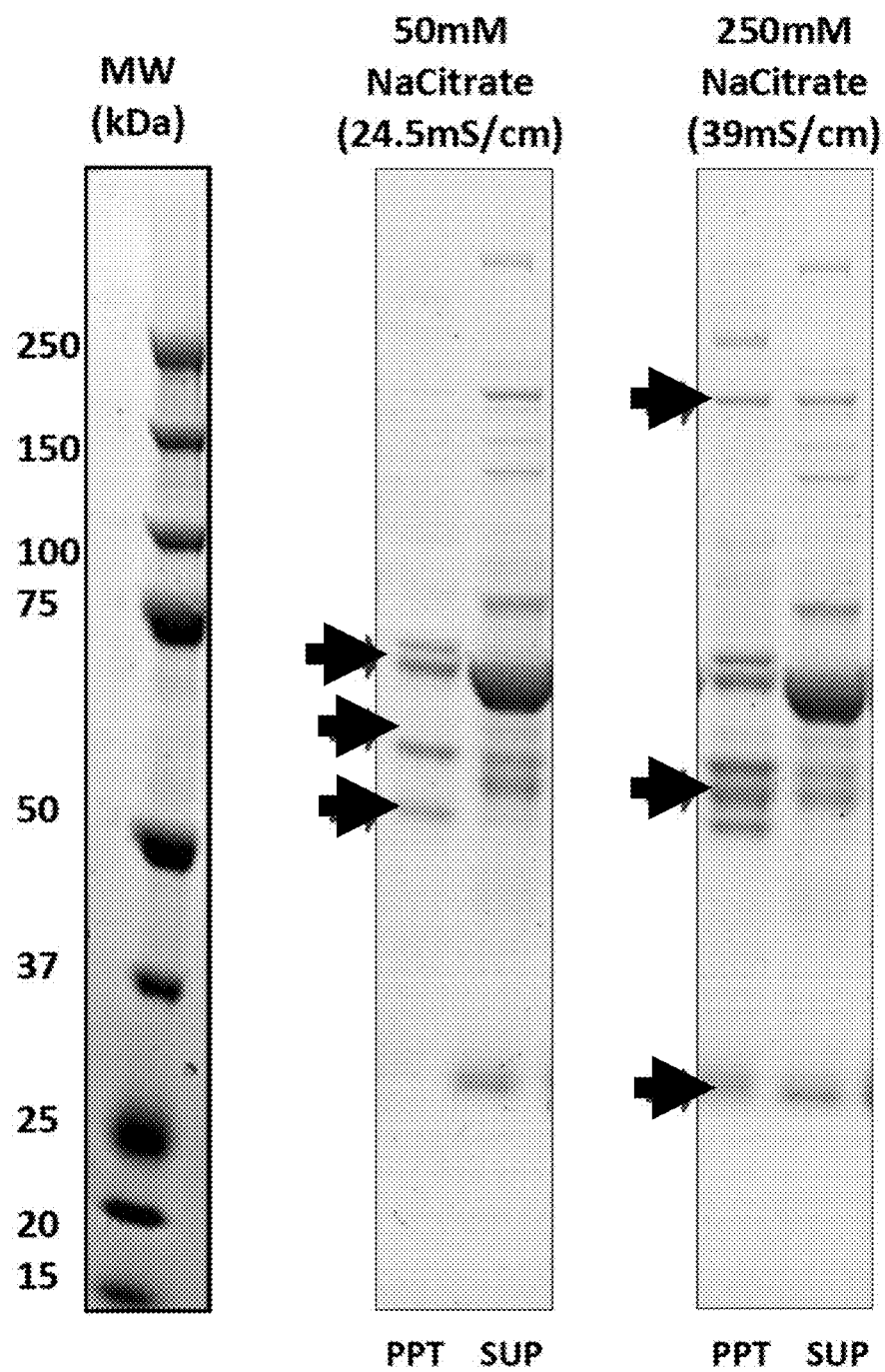
FIG. 14. 1D reduced SDS gel electrophoresis of plasma protein fractionation in 5% (w/w) PAA 15 000 containing 5 ml system with 1.5 ml added plasma plus 50 or 250 mM NaCitrate, pH 7. Arrows indicate the appearance of new prominent protein bands in the precipitate samples.

The influence of the conductivity on the selectivity of fractionating of plasma proteins with polyacid and lyotropic salt systems was investigated. The conductivities of systems with varying concentrations of NaCitrate buffer, NaCl and polyacrylic acid of 15000 MW (PAA) were measured in various pH 7 systems (Table 7 and FIG. 13). The conductivity of the systems increases directly with PAA concentration (FIG. 13). As expected, the effects of PAA concentration on system conductivity are more apparent at lower added salt concentration, and the effects of added salt on system conductivity are more apparent at lower PAA concentration. When 1.5 ml plasma is precipitated in 5 ml total volume system containing 10% PAA 15000 electrophoretic analysis of the precipitate and supernatant fractions suggests there is little change in conductivity, or protein distribution between the fractions, when going from 100 mM NaCitrate (39.8 mS/cm) to 200 mM NaCitrate (42.8 mS/cm). However in systems containing 5% PAA there is a significant change in both conductivity and protein distribution on going from 50 mM NaCitrate (24.5 mS/cm) to 250 mM NaCitrate (39.0 mS/cm) with more protein bands appearing in the precipitate fraction electrophoresis gels (FIG. 14). Thus it appears that the general approach is very robust in regard to slight variation in conductivity and, at least at lower polyacid concentrations, the selectivity of protein precipitation can be partially controlled varying the salt composition in the precipitation solution (see also Example 9).

The above results suggest that while salt concentration may be used to fine tune selectivity in fractionation process based on varying polyacid concentration (per Example 7) it may also be possible to develop a process where polyacid concentration is kept constant and salt concentration is increased in steps. Data supporting this is presented in Example 9.

TABLE 7

The conductivity of systems with varying concentrations of NaCitrate, NaCl and PAA 15000.

| System | NaCitrate/NaCl (mM) | Conductivity (mS/cm)* 4% w/w PAA | w/w 10% PAA |
|---|---|---|---|
| 1 | 50/50 | 25.8 | 38.7* |
| 2 | 250/50 | 41.5 | 46 |
| 3 | 50/200 | 34.9 | 44.2 |
| 4 | 250/200 | 47.8 | 50.7 |
| 5 | 50/0 | 24.5 | n/a |
| 6 | 100/0 | n/a | 39.8 |
| 7 | 150/0 | n/a | 41 |
| 8 | 200/0 | n/a | 42.8 |
| 9 | 250/0 | 39 | n/a |

*The conductivity for system 1 without PAA was 16.8 mS/cm and with 8% (w/w) PAA it was 33.5 mS/cm.

Figure 15:
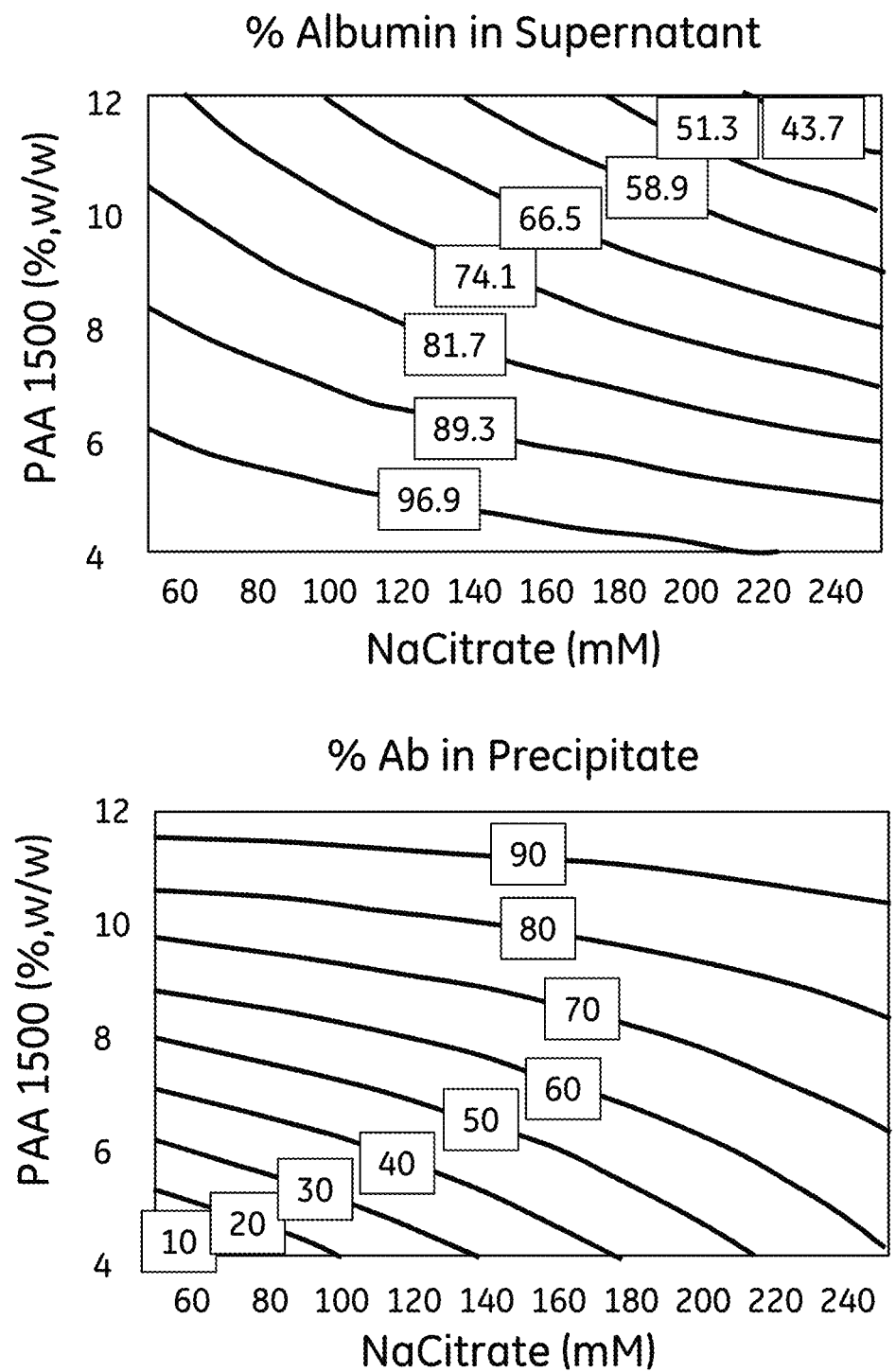
FIG. 15. Results from cubic centered face (CCF) design of experiments study where concentration % w/w of PAA 15 000 and mM concentration of NaCitrate, were varied in 5 ml system containing 200 mM NaCl in order to optimise conditions where antibody or albumin could be selectively precipitated.

Example 9. Suitability to Optimize Via High Throughput Screening and Design of Experiments Standard cubic centered face (CCF) design of experiments (DOE) was used together with small scale (5 ml) experiments to further investigate the ability of varied concentrations of PAA 15000 (4-12%) and NaCitrate (50 to 250 mM) to effect selectivity in inclusion of albumin and antibody in precipitates in systems containing 1.5 ml plasma and NaCl at either 0 mM to 200 mM. Example results at 200 mM NaCl are shown in FIG. 15. At higher PAA (12%) and increased NaCitrate to 250 mM it is estimated that 56% of the albumin which is present is in the precipitate together with more than 90% of the antibody. As NaCitrate is decreased to 60 mM antibody precipitation is still close to 90% however only 25% of the albumin is in the precipitate. The ease with which the general polyacid-lyotropic salt methodology can be adapted to such rapid screening, and the selectivity control it should allow, support the commercial potential of the method.

Example 10. Effect of pH

Figure 16:
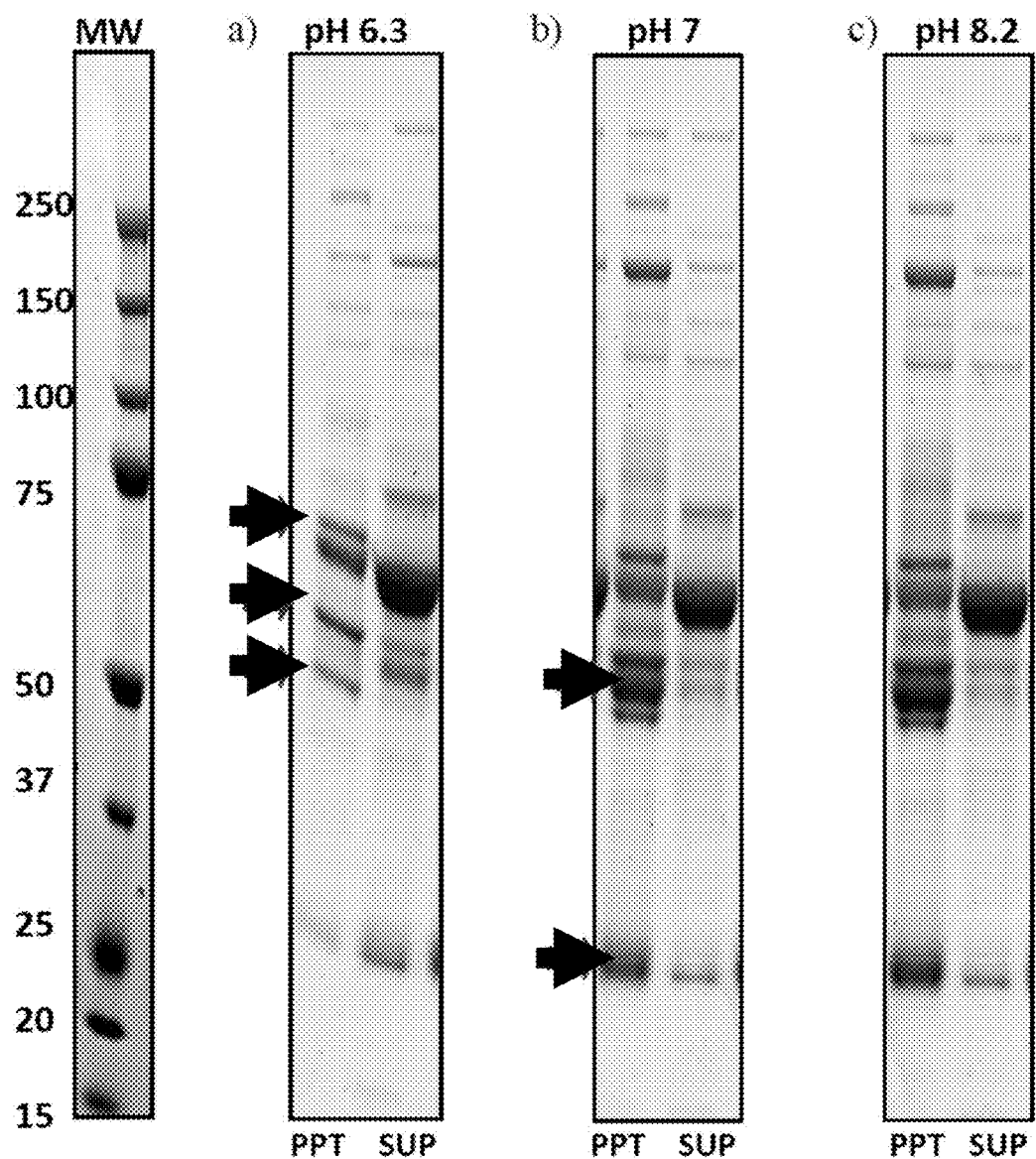
FIG. 16. Effect of pH on plasma protein fractionation in 5 ml system containing 8% (w/w) PAA 15 000, 50 mM NaCl and 50 mM NaCitrate final system pH 6 to 8. Arrow indicates a new prominent band in the precipitate.

To investigate the effect of system pH, stock solutions of NaCitrate (0.8M) were prepared at pH 3, 5, 7 and 9. NaCitrate was added reach 50 mM in equal systems with 8% (w/w) PAA and 50 mM NaCl. Due to the pH of plasma and water and the pKa of citrate the pH in the final systems increased to 6.3, 7, 8.2 and 8.3 respectively. The pH effect on protein precipitation was analysed with 1D SDS-PAGE (and GelCode Blue Coomassie staining) (FIG. 16) and those results combined with Biuret assay (total protein) plus ImageQuantTL (PAGE gel band analysis of relative protein amounts) to provide an estimate of the percentage of individual proteins (albumin, antibody and fibrinogen) in the precipitates. The almost total incorporation of fibrinogen and relatively low level incorporation of albumin into precipitate in the above system was little affected by pH alteration from 6 to 8. However antibody incorporation into the precipitate increased directly with pH (data not shown). The precipitation of some other unassigned proteins of higher MW were also influenced by pH (FIG. 16). Therefore pH may possibly be used to fine tune fractionation of certain proteins by the general method. Little change in antibody precipitation per gel appearance between pH 8.2 and 8.3 again suggests method robustness.

In the present example system with relatively low concentration of NaCitrate was used and this limited the buffering capacity of the system and the pH range studied. Cohn Fractionation can involve varying of pH from 4 to 8 (ref. 16, see also FIG. 1). It may be possible to vary pH over wider range if higher concentration of chaotropic buffering salt (e.g. NaCitrate or NaPhosphate) is used or if another buffering system is employed in combination with any required lyotropic salt.

Considering the isoelectric pH ranges of the proteins studied (Table 1) it is expected that under the conditions studied in this example (i.e. pH 6 to 8) albumin should be net negatively charged and remain negatively charged, fibrinogen should be predominantly net negatively charged, and different antibodies typically found in the plasma (pI range 6 to 10) may be neutral, net negative or net positive charged. Many other plasma proteins such as transferrin and factor VIII are also expected to be primarily neutral or net negative in the pH range studied. The electrophoresis results therefore indicate that in case of fibrinogen the general methodology is able to precipitate net negatively charged proteins, as well as net positively charged antibodies. Furthermore as pH is increased and various antibody proteins appear to become less net positively charged their complexation appears to increase. This is counter-intuitive to an approach which is just based on charge-charge interaction of net negatively charged polymer with net positively charged protein. It could be related to significant role of protein solubility (surface hydrophobicity) as well as protein-salt and protein-protein interactions. The precipitation appears to be a result of combination of a variety of phenomena and, without being bound by theory, it is speculated that protein size, relative surface hydrophobicity and other factors (e.g. surface regions of net positive nature) may play a role. Regardless of the mechanisms involved under the conditions studied the polyacid PAA is able to mediate complex formation with proteins which may be net negative, net positive or neutral.

Example 11. Effects of Centrifugation, Temperature, and Salt Addition

Some variables of interest in regard to practical, larger-scale, application of the general methodology were also investigated. These included centrifugation speed and time, addition of citrate as salt rather than in stock solution, and variation in temperature.

It is assumed that any flocculate/precipitate will be recovered by centrifugation or filtration. In the present work centrifugation was used pellet down the precipitate to be able to separate it from the supernatant. Centrifugation of 5 ml or smaller volumes was performed at 4000 revolutions per minute (rpm) for 10 minutes (see Methods above) with successful results. Equally successful results were obtained at 4000 rpm for 5 minutes or even and at 2000 rpm for 5 minutes. In these studies the precipitates were well isolated and recovered and the 1D SDS gel electrophoresis analysis indicated no change in precipitate or supernatant samples for 5 ml systems containing 1.5 ml plasma, 50 mM NaCl and 50 mM NaCitrate pH 7 (data not shown). These results also suggest that the polymer-protein complexes are both dense and mechanically robust enough to handle filtration or other possible approaches.

It could be advantageous to add salts as solids rather than as stock solutions. Thus in one experiment involving 5 ml system with 1.5 ml plasma plus final concentration of 8% PAA and 200 mM NaCitrate the citrate was added as salt crystals instead of from stock solution (see Methods above). Precipitation occurred in an apparently normal fashion and 1D SDS gel electrophoresis analysis of the precipitate and supernatant fractions showed reasonably similar results (data not shown).

Figure 17:
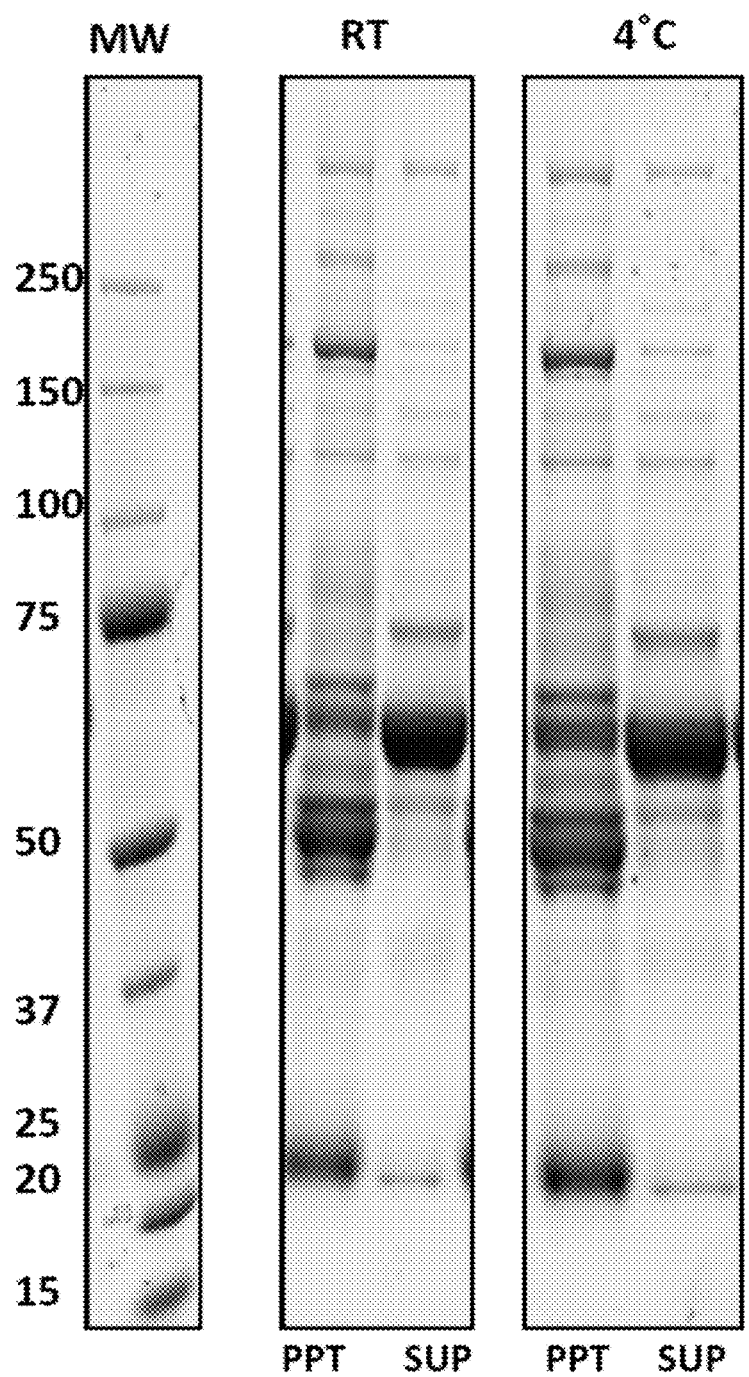
FIG. 17. Effect of temperature on plasma precipitation in 5 ml system containing 1.5 ml plasma plus 8% PAA 15 000, 50 mM NaCl and 50 mM NaCitrate, pH 7.

PAA precipitate-related experiments were generally performed at 22° C. (room temperature). However in Cohn Fractionation based plasma processing frozen plasma will be thawed to 4° C. (which effects first fractionation of plasma, see also refs. 15,16). Thereafter the solution temperature may be varied to add selectivity to various fractionation steps. Even for an isothermal PAA-precipitation based process it may be desirable to perform the process at 4° C. Therefore, one system was prepared with plasma at 4° C. and the sample was kept at 4° C. during the precipitation. No significant difference could be seen when compared with a precipitate or supernatant samples prepared at 22° C. (FIG. 17).

Example 12. Sequential Precipitation of Non-Diluted Plasma

Frozen pooled Heparinized Plasma was thawed in luke warm water. 10 g of plasma was mixed in a 15 ml Falcon tube with poly acrylic acid (35% solution in water, Aldrich 411637-500 ml, MW 15000)

The mixtures was left standing on the lab bench 1 h at RT

The mixtures was spun at 500 g, 10 min in a Eppendorf table centrifuge at Room temperature.

The clear top solution was diluted and A280 was measured. The results are shown in Table 8.

TABLE 8

Results from first precipitation series.

| Sample | Mix Blood:PAA (g) | Final % PAA | Dilution, A280 | A280 in original sample | % of original |
|---|---|---|---|---|---|
| Blood plasma | 10:0 | 0 | 101, 0.524 | 53 | 100 |
| Blood plasma | 10:0 | 0 | 101, 0.543 | 55 | 100 |
| 5% PAA | 10:1.6 | 5 | 101, 0.464 | 47 | 87 |
| 5% PAA | 10:1.6 | 5 | 101, 0.472 | 48 | 88 |
| 10% PAA | 10:3.7 | 10 | 101, 0.313 | 32 | 60 |
| 10% PAA | 10:3.7 | 10 | 101, 0.322 | 32 | 60 |

10% PAA was not enough to precipitate all proteins (A280 adsorbing compounds) in the plasma.

Hence, a second run was performed, increasing the PAA concentration further up to 20%. The results from this run are shown in Table 9.

| Sample | Mix Blood:PAA (g) | Final % PAA | Dilution, A280 | A280 in original sample | % of original |
|---|---|---|---|---|---|
| Plasma | 100:0 | 0 | 101, 0.533 | 54 | 100 |
| 15% PAA | 10:7.5 | 15 | 101, 0.150 | 15 | 28 |
| 20% PAA | 10:13.5 | 20 | 101, 0.110 | 11 | 20 |

With PAA concentrations as high as 15 and 20%, most of the plasma proteins were precipitated.

At these concentrations, the pH increased about 1 unit, so a pH adjustment during processing can be beneficial for stability of some sensitive plasma proteins. An interesting observation was also that the precipitates obtained with 15 and 20% PAA floated on top of the liquid phase. This can have advantages for the recovery of the precipitate.

This written description uses examples to disclose the invention, including the best mode, and also to enable any person skilled in the art to practice the invention, including making and using any devices or systems and performing any incorporated methods. It is pointed out that the specific advantageous embodiments of the various aspects of the invention disclosed above can be freely combined to further embodiments within the scope of the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A process for separating at least fibrinogen and immunoglobulin G from a sample of blood plasma, comprising the steps of:
   a) providing a sample of blood plasma in a container;
   b) adding a polyacid and a salt comprising ≤50 mM sodium chloride and at least one additional salt to the blood plasma, whereby said blood plasma comprises 50-100 mmol/L of total salt at pH between 6 and 8, causing formation of a first protein precipitate that comprises a majority of the fibrinogen in said sample and recovering said first protein precipitate and a first supernatant separately; and
   c) adding an additional amount of a polyacid to said first supernatant, causing formation of a second protein precipitate that comprises a majority of the immunoglobulin G in said sample and a second supernatant and recovering said second protein precipitate separately, wherein the polyacid is added in an amount to give a total polyacid concentration in said first supernatant which is 5-8%;
   wherein said first protein precipitate comprises a concentrate of the first protein and said second protein precipitate comprises a concentrate of the second protein.

2. The process of claim 1, wherein said polyacid is selected from the group consisting of polyacrylic acid, polymethacrylic acid, polyvinylsulfonic acid, polystyrenesulfonic acid, carboxymethyl dextran and carboxymethyl cellulose.

3. The process of claim 1, wherein said additional salt is selected from the group consisting of sodium phosphates, potassium phosphates, ammonium phosphates, sodium citrates, potassium citrates, ammonium citrates, sodium sulphates, potassium sulphates, ammonium sulphates, sodium acetate, potassium acetate, ammonium acetate or any combination thereof.

4. The process of claim 1, wherein the temperature in steps b) and/or step c) is between 0 and 40° C.

5. The process of claim 1, wherein in step c) the second protein precipitate comprises essentially all the remaining proteins from the blood plasma.

6. The process of claim 1, wherein step c) further comprises recovering a second supernatant and further comprising a step d) of adding a polyacid and/or a salt to said second supernatant, causing formation of a third protein precipitate comprising a concentrate of a third protein and recovering said third protein precipitate.

7. The process of claim 6, wherein said third protein is albumin.

8. The process of claim 1, wherein said blood plasma is human blood plasma or animal blood plasma.

9. The process according to claim 1, further comprising a step of pathogen inactivation or removal.

10. The process of claim 1, wherein at least one protein precipitate is redissolved and subjected to a further step such as precipitation, crystallisation, chromatography, and/or filtration for separation of said first, second and/or third protein.

11. The process of claim 1, wherein step a) is preceded by a step a') of separating blood cells from blood by aqueous two-phase separation.

12. The process of claim 11, wherein step a') comprises the substeps of:
    i) adding a self-associating responsive polymer, and optionally a salt, to a sample of blood;
    ii) increasing the temperature or adding salt, causing the formation of a polymer rich aqueous phase, a polymer poor aqueous phase and a phase interface comprising blood cells; and
    iii) recovering the polymer poor aqueous phase as the blood plasma.

13. The process of claim 12, wherein the total responsive polymer content in step ii) constitutes about 4-20 wt % of the total system.

14. The process of claim 12, wherein pH in step ii) is between 6 and 8.

15. The process of claim 12, wherein the concentration of added salt in step ii) is in the range of 1-500 mmol/L.

16. The process of claim 12, wherein the salt is selected from the group consisting of sodium chloride, sodium phosphates, potassium phosphates, sodium sulphate, potassium citrates, sodium citrates, ammonium sulphate and sodium acetate; or any combination thereof.

17. The process of claim 12, wherein in substep i) or ii) 1-10 wt % ethanol is added to the blood.

18. The process of claim 12, wherein the self-associating responsive polymer exhibits a cloud point between 2 and 100° C. and is optionally selected from the group consisting of ethylene oxide—propylene oxide copolymers and ethylhydroxyethylcellulose.

19. The process of claim 12, wherein the self-associating responsive polymer has a weight average molecular weight of 0.9-100 kDa.

20. The process of claim 12, wherein step a') is run in a continuous mode.

21. The process of claim 12, wherein step a') is performed in plastic containers.

22. The process of claim 21, wherein the self-associating responsive polymer, and optionally the salt, are present in the plastic containers before introduction of the blood in the containers.

23. The process of claim 12, wherein said polymer poor aqueous phase is freeze dried or stored for at least one day or one week at a temperature below 8° C.

24. The process of claim 12, wherein said first and second proteins are suitable for use as pharmaceuticals.

25. The process of claim 12, wherein stabilizers, anti-aggregation agents and/or anti-proteolytic agents are added to the aqueous phases to promote storage and recovery of active target in a native functioning state.

* * * * *